(12) United States Patent
Hoyt et al.

(10) Patent No.: US 11,548,858 B2
(45) Date of Patent: Jan. 10, 2023

(54) BIODERIVED EPOXIDE TRIAZINE NETWORKS AND METHODS OF MAKING THE SAME

(71) Applicant: Alliance for Sustainable Energy, LLC, Golden, CO (US)

(72) Inventors: Caroline Bradshaw Hoyt, Denver, CO (US); Nicholas A. Rorrer, Golden, CO (US); Gregg Tyler Beckham, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 112 days.

(21) Appl. No.: 17/324,222

(22) Filed: May 19, 2021

(65) Prior Publication Data

US 2021/0363114 A1 Nov. 25, 2021

Related U.S. Application Data

(60) Provisional application No. 63/026,891, filed on May 19, 2020.

(51) Int. Cl.
*C07D 251/04* (2006.01)

(52) U.S. Cl.
CPC .................. *C07D 251/04* (2013.01)

(58) Field of Classification Search
CPC ................................................... C07D 251/04
See application file for complete search history.

(56) References Cited

U.S. PATENT DOCUMENTS 3,383,434 A  5/1968 Carlston

OTHER PUBLICATIONS

You et al., Hexahydro-s-triazine: Atrial for Acid-Degradable Epoxy Resins with High Performance, ACS Sustainable Chemistry & Engineering, vol. 5, Issue 6, pp. 4683-4689 (2017).*
CN105440261 (WIPO Machine Translation) (2016).*
CN106905252 (WIPO Machine Translation) (2017).*
Ali et al., "Synthesis of thermotropic polybenzoxazole using 3-amino-4-hydroxybenzoic acid", Journal of Polymer Research, 2017, vol. 24, No. 214, pp. 1-7.
Barton, "Monitoring the Curing Reaction of an Aromatic Amine/Epoxide Resin System by Differential Scanning Calorimetry (DSC): Determined and Significance of the Activation Energy, "Die Makromolekulare Chemie, 1973, vol. 171, pp. 247-251.
García et al., "Recyclable, Strong Thermosets and Organogels via Paraformaldehyde Condensation with Diamines", Science, May 2014, vol. 344, pp. 732-735.
Mirzakhanian et al., "Synthesis of Bio-Based Polyamide/Acid-Functionalized Multiwalled Carbon Nanotube Nanocomposites Using Vanillin", Polymer-Plastics Technology and Engineering, 2018, vol. 57, No. 13, pp. 1367-1376.
Koelewijn et al., "Sustainable bisphenols from renewable softwood lignin feedstock for polycarbonates and cyanate aster resins", Green Chemistry, 2017, vol. 19, pp. 2561-2570.
Koelewijn et al., "Promising bulk production of a potentially benign bisphenol A replacement from a hardwood lignin platform", Green Chemistry, 2018, vol. 20, pp. 1050-1058.
Xu et al., "Recyclable thermoset hyperbranched polymers containing reversible hexahydro-s-triazine", Nature Sustainability, Jan. 2002, vol. 3, pp. 29-34.
Zhao et al., "Renewable Epoxy Networks Derived from Lignin-Based Monomers: Effect of Cross-Linking Density", ACS Sustainable Chemistry & Engineering, 2016, vol. 4, pp. 6082-6089.

* cited by examiner

*Primary Examiner* — Deepak R Rao
(74) *Attorney, Agent, or Firm* — Michael A. McIntyre

(57) ABSTRACT

The present disclosure relates to a method that includes a first reacting of a first molecule and formaldehyde and/or a paraformaldehyde to form a triazine-containing intermediate and a second reacting of the triazine-containing intermediate with a second molecule having an epoxy group to form a triazine-containing product. As described herein, the triazine-containing product may be bioderived and biodegradable.

20 Claims, 6 Drawing Sheets

BIODERIVED EPOXIDE TRIAZINE NETWORKS AND METHODS OF MAKING THE SAME

CROSS-REFERENCE TO RELATED APPLICATIONS

This application claims priority from U.S. Provisional Patent Application No. 63/026,891 filed on May 19, 2020, the contents of which is incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Industry continues to use bisphenol A (BPA) as a monomer for producing polymers and resins. The derivation from lignin of bioderived alternatives has the potential to alleviate dependence on the petroleum industry for the production of such materials, which could then eliminate the adverse health and environmental effects resulting from the use of BPA. Thus, there remains a need for improved reactants and methods for making useful and cost-effective bioderived, intermediates, polymers, and resins.

SUMMARY

An aspect of the present disclosure is a method that includes a first reacting of a first molecule and formaldehyde and/or a paraformaldehyde to form a triazine-containing intermediate and a second reacting of the triazine-containing intermediate with a second molecule having an epoxy group to form a triazine-containing product. The first molecule has a structure that includes

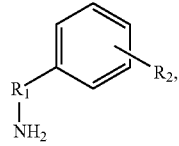

the triazine-containing intermediate has a structure that includes

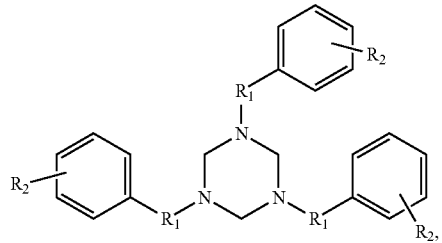

the second molecule has a structure that includes

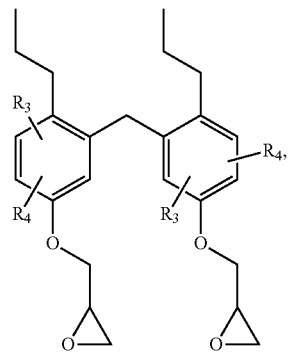

and the triazine-containing product has a structure that includes

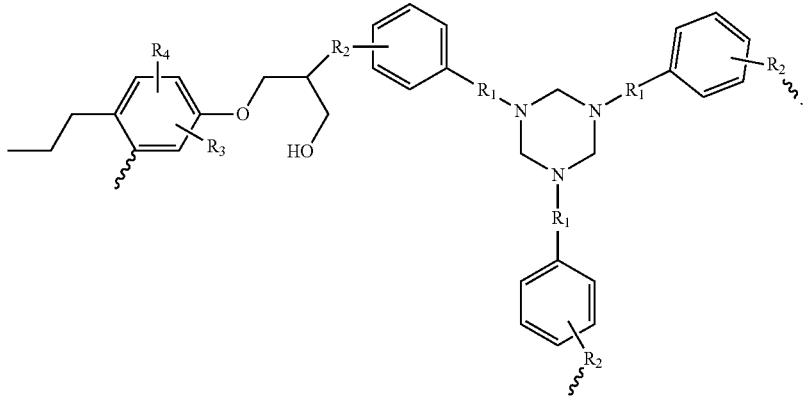

$R_1$ includes at least one of a covalent bond and/or an alkyl having between 1 and 4 carbon atoms, $R_2$ is derived from at least one of an amine group, an amide group, an ester group, and/or a carboxylic acid group, $R_3$ includes at least one of an alkoxy group, a hydroxyl group, an epoxide group, and/or a methylene group, $R_4$ includes at least one of an alkoxy group, a hydroxyl group, an epoxide group, and/or a methylene group, and ⌇ represents a covalent bond to a neighboring atom. In some embodiments of the present disclosure, $R_2$ may further include an alkyl group.

In some embodiments of the present disclosure, the structure of the triazine-containing product may further include

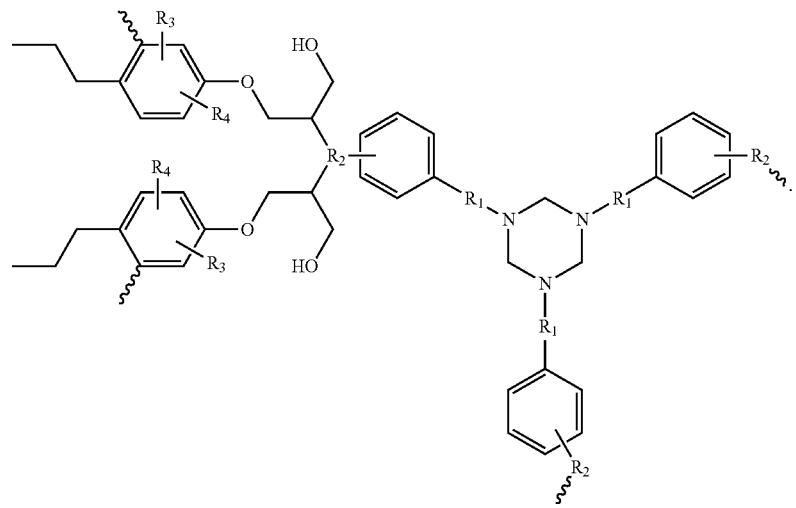

In some embodiments of the present disclosure, the structure of the triazine-containing product may further include

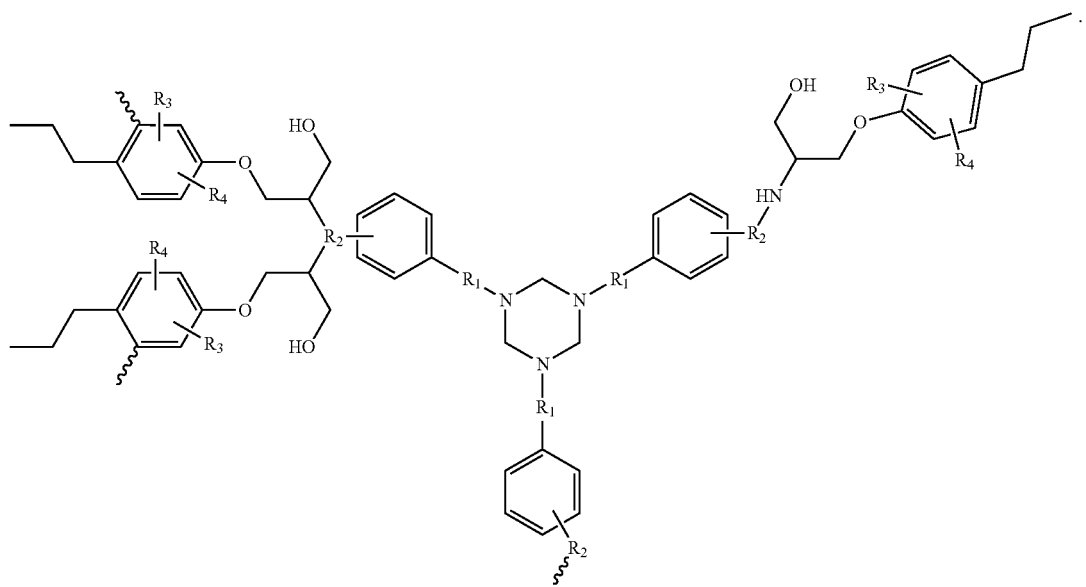

In some embodiments of the present disclosure, the structure of the triazine-containing product may further include

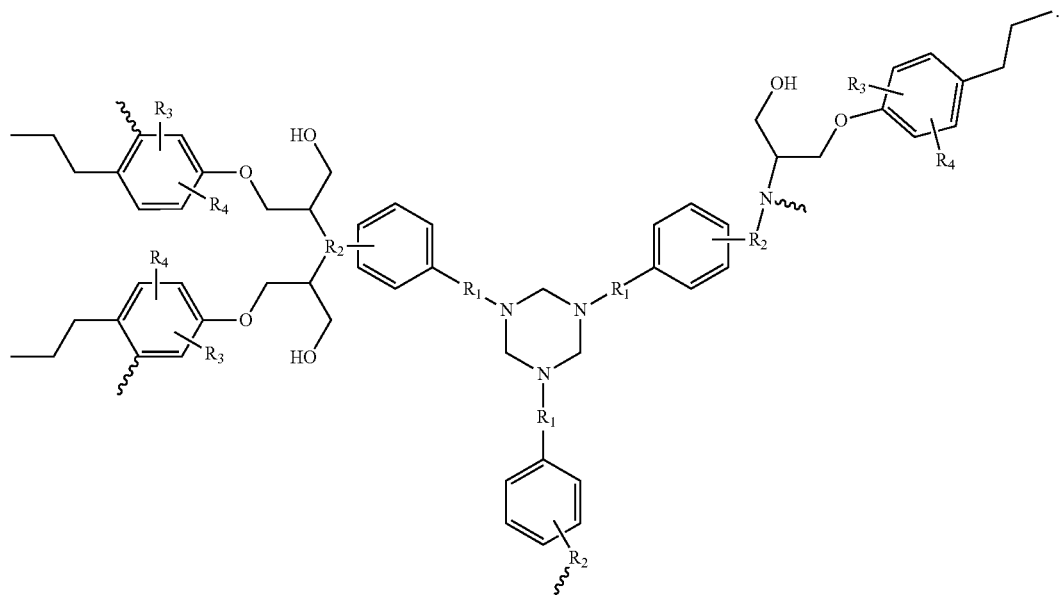

In some embodiments of the present disclosure, the structure of the first molecule may include

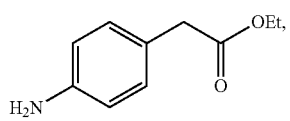

and the structure of the triazine-containing intermediate may include

In some embodiments of the present disclosure, the method may further include a third reacting of the triazine-containing intermediate with a diamine, where the diamine has a structure that includes $H_2N-R-NH_2$, the third reacting transforms the triazine-containing intermediate to a structure that includes

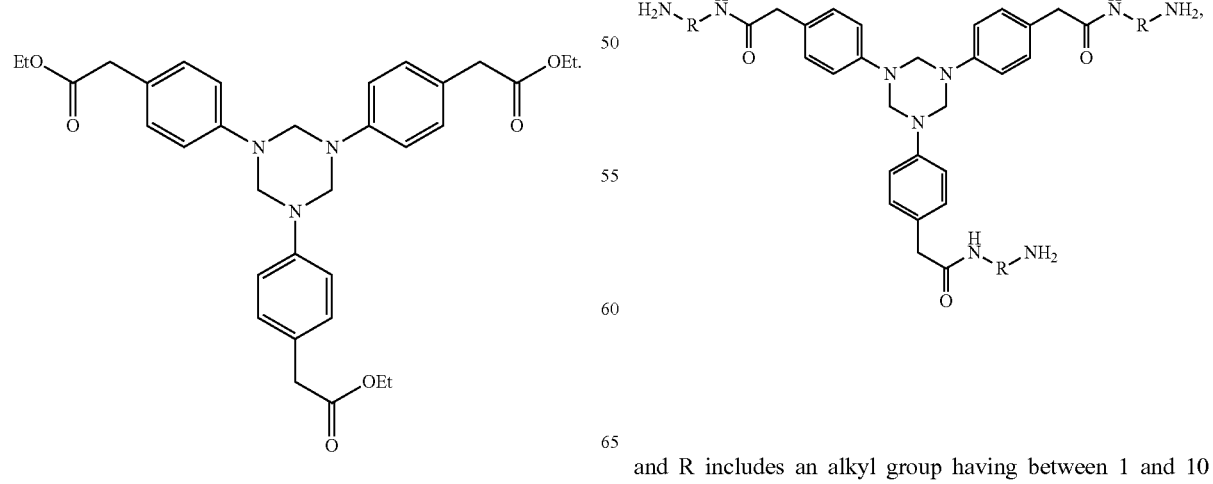

and R includes an alkyl group having between 1 and 10 carbon atoms.

In some embodiments of the present disclosure, the second reacting may form the triazine-containing product having a structure that includes

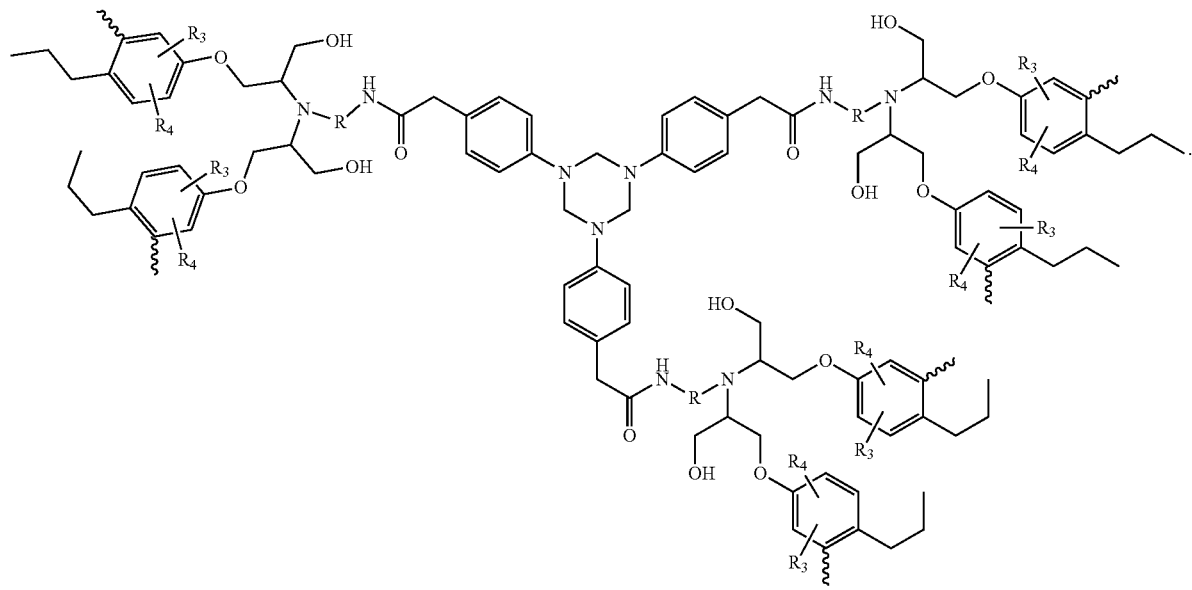

In some embodiments of the present disclosure, the method may further include a fourth reacting of the triazine-containing intermediate with a base, where the fourth reacting transforms the triazine-containing intermediate to a structure that includes

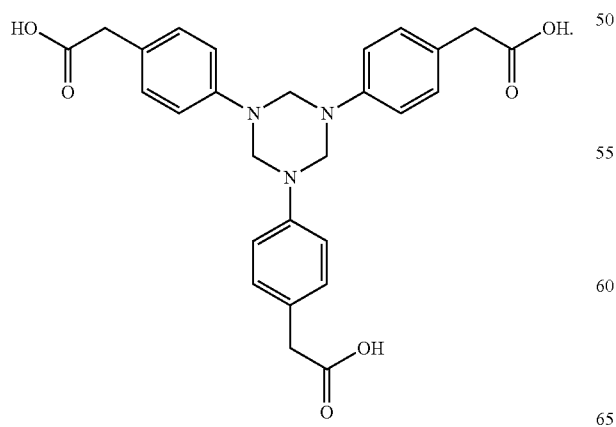

In some embodiments of the present disclosure, the second reacting may form the triazine-containing product having a structure that includes

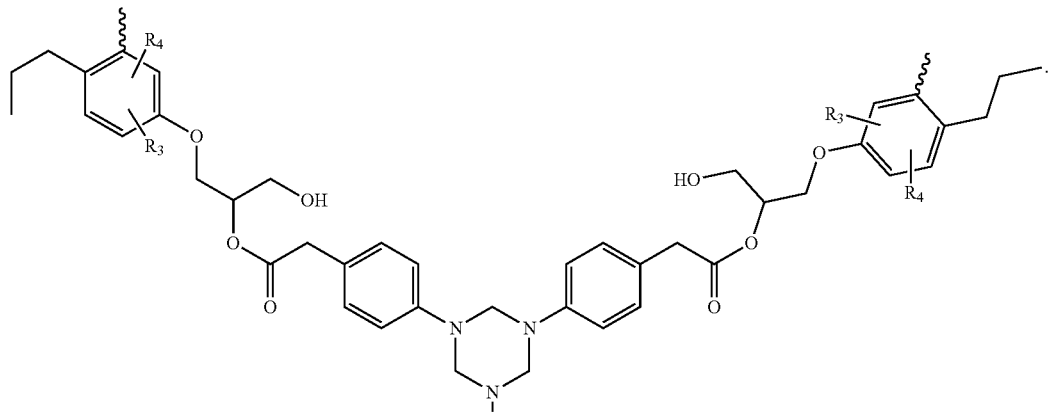

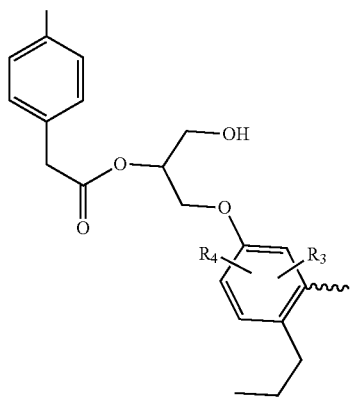

In some embodiments of the present disclosure, at least one of the first molecule and/or the second molecule may be bioderived. In some embodiments of the present disclosure, the triazine-containing produce may be biodegradable.

An aspect of the present disclosure is a composition that includes the structure

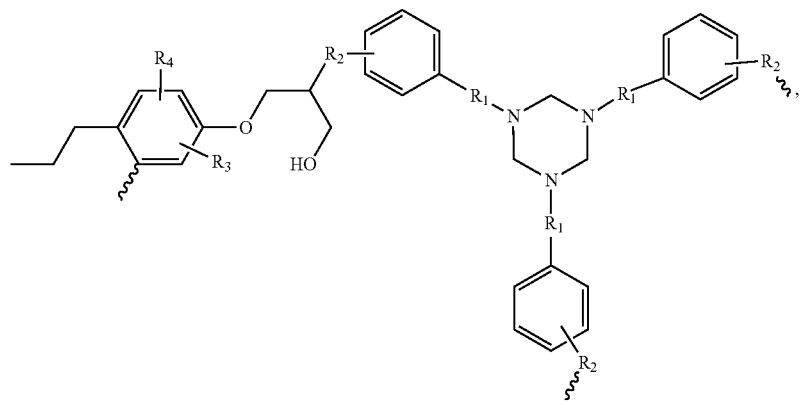

where $R_1$ includes at least one of a covalent bond and/or an alkane having between 1 and 4 carbon atoms, $R_2$ includes at least one of an amine group, an amide group, an ester group, and/or a carboxylic acid group, $R_3$ includes at least one of an alkoxy group, a hydroxyl group, an epoxide group, and/or a methylene group, $R_4$ includes at least one of an alkoxy group, a hydroxyl group, an epoxide group, and/or a methylene group, and ⌇ represents a covalent bond to a neighboring atom.

In some embodiments of the present disclosure, the structure may further include

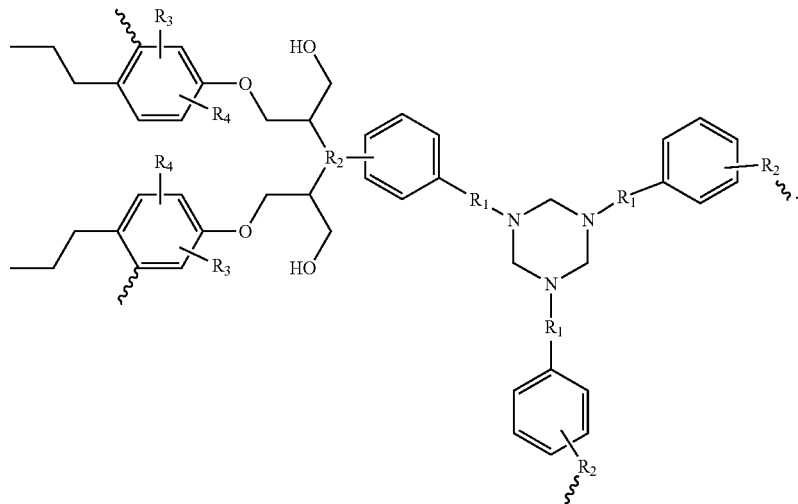

In some embodiments of the present disclosure, the structure may further include

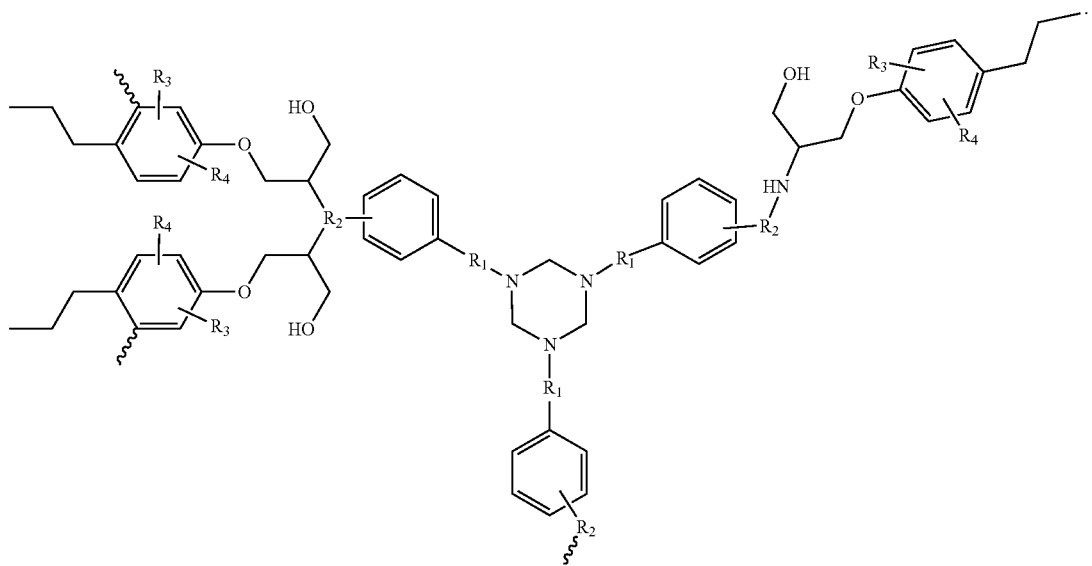

In some embodiments of the present disclosure, the structure may further include
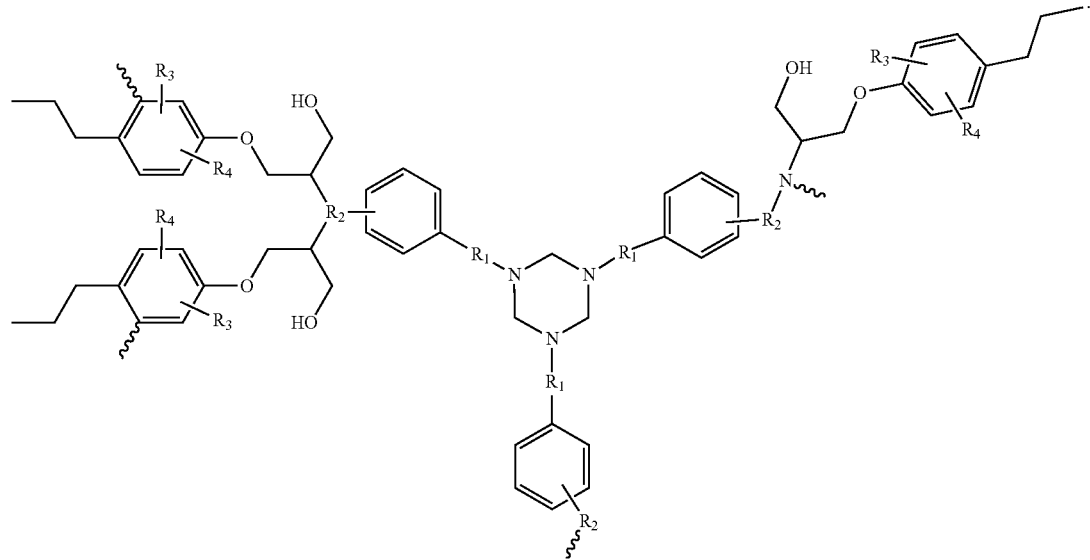
In some embodiments of the present disclosure, the structure may include
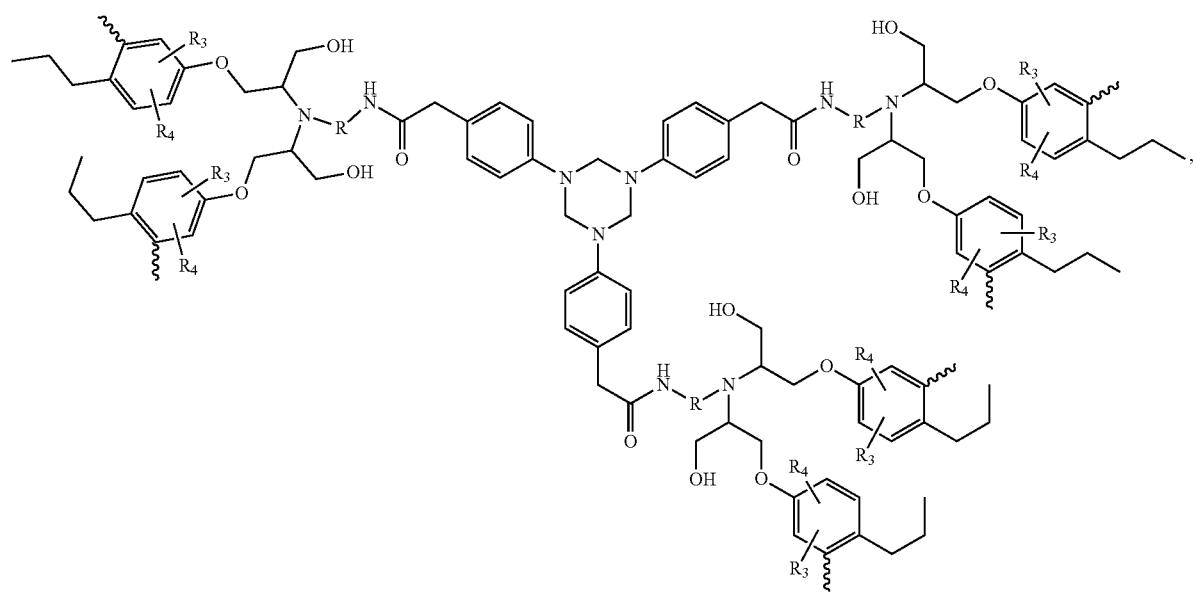
where R includes an alkyl group having between 1 and 10 carbon atoms.

In some embodiments of the present disclosure, the structure may include

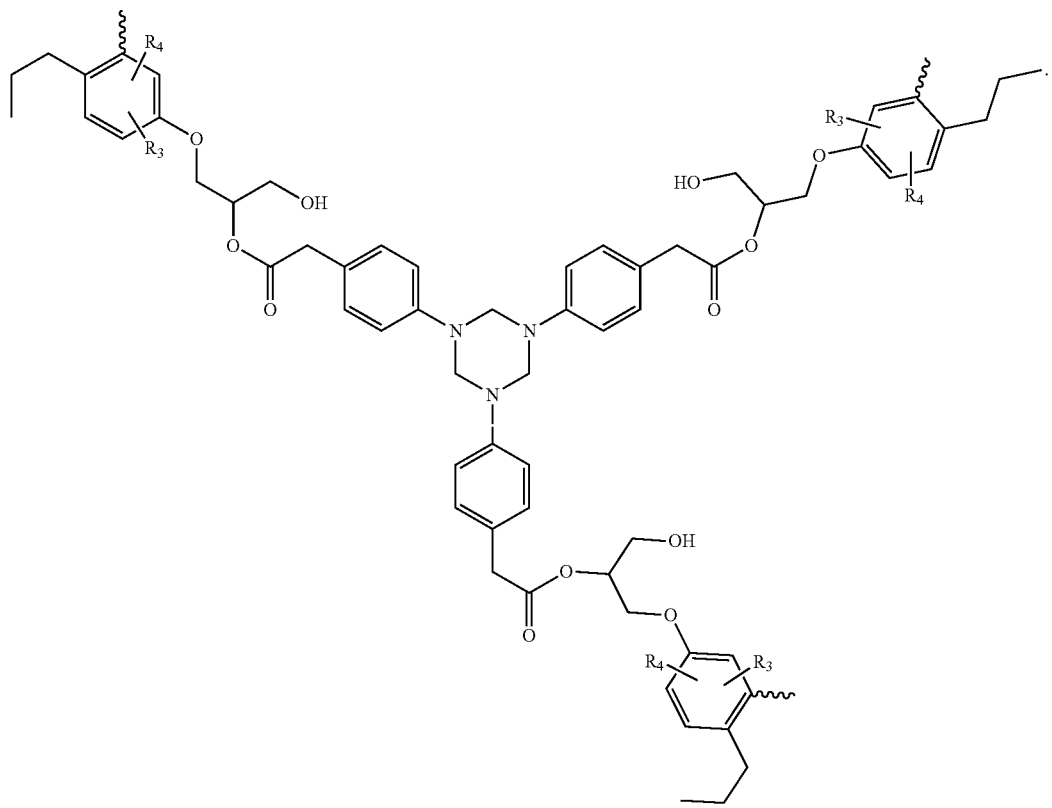

In some embodiments of the present disclosure, at least a portion of the composition may be bioderived. In some embodiments of the present disclosure, the composition may be biodegradable.

BRIEF DESCRIPTION OF THE DRAWINGS

Some embodiments are illustrated in referenced figures of the drawings. It is intended that the embodiments and figures disclosed herein are to be considered illustrative rather than limiting.

DETAILED DESCRIPTION

Figure 1:
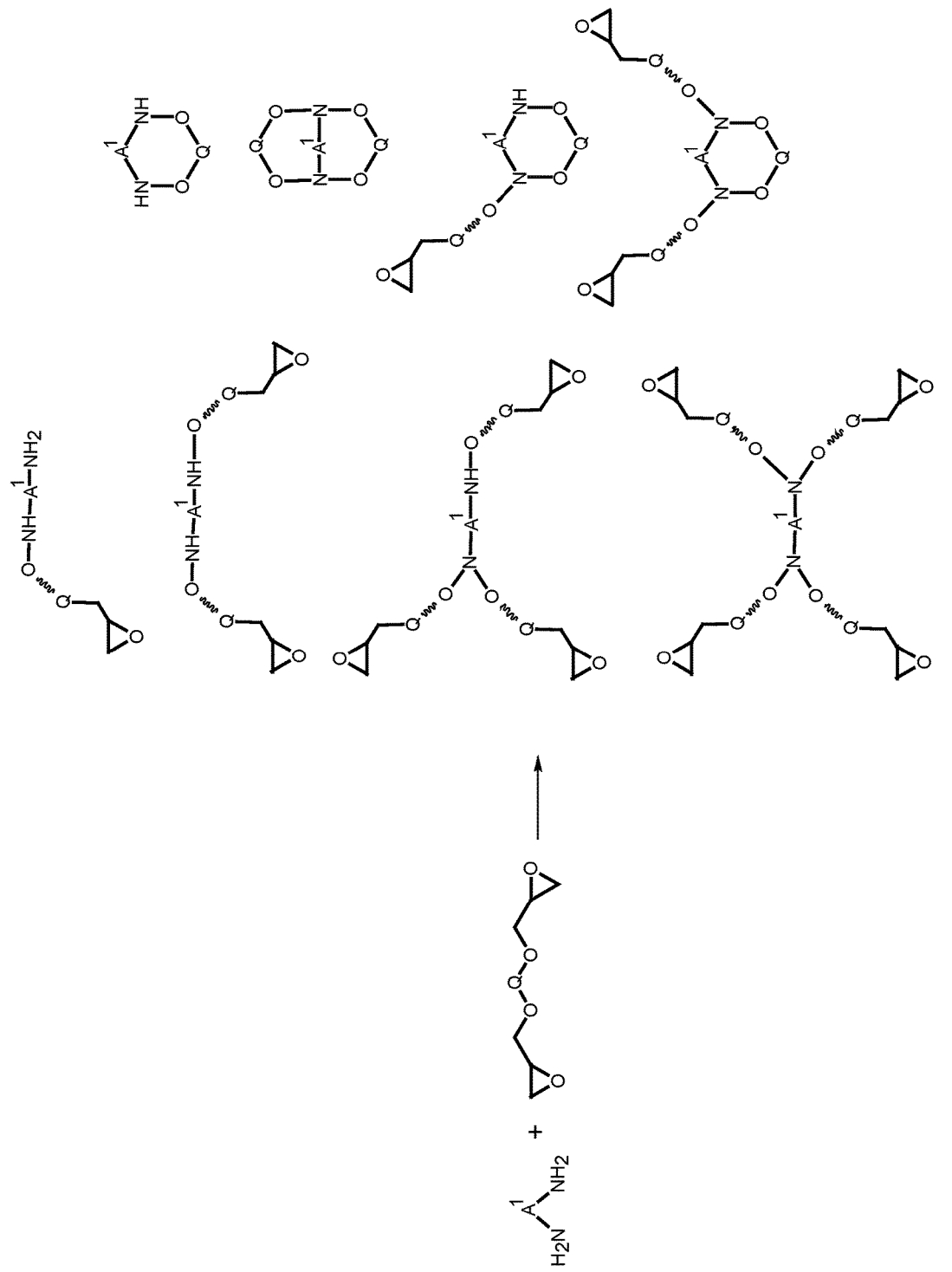
FIG. 1 illustrates a reaction of a diamine with an epoxy-containing molecule for producing a variety of larger molecules, which may be incorporated into a resin, according to some embodiments of the present disclosure.

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

Among other things, the present disclosure relates to resins based on the reacting of bioderived amine-functionalized compounds with epoxy-functionalized compounds, where the resultant resins contain triazine linkages. The triazine linkages may, among other things, provide a handle for degrading, recovering, and/or recycling the materials originally utilized to produce the resins, at a product's end-of-life. As shown herein, in some embodiments of the present disclosure, monomers and/or dimers having epoxide groups and/or amine groups, derived from the degradation of lignin, may be reacted to produce degradable, bioderived resins. Although the focus of the present disclosure is the synthesis of bioderived resins, petroleum-derived monomers may also be utilized to produce the degradable resins described herein and are considered within the scope of the present disclosure.

Epoxide resins may be modified to improve thermal and mechanical properties. Further, triazine networks can provide excellent thermal and mechanical strength. As described herein, bioderived diamines may be used to synthesize these triazine linkages and incorporate them into a final degradable resin. First, the amine groups of more than one diamine molecules may react with an aldehyde (e.g., formaldehyde) to form nitrogen-containing, amine-functionalized heterocycles, including triazines, diazines, and/or tetrazines. Subsequently, the amine groups on the heterocycles, in addition to the amine groups of the starting diamine, may further react with the epoxide functional groups of the second reactant, thereby forming a resin network constructed of triazine, diamine, and epoxide-functionalized building blocks. Among other things, the triazine groups may provide degradation sites that may deconstruct in the presence of a strong acid. This would address the needs for degradable thermoset networks, as well as reduce the dependency on bisphenol A (BPA) materials which have been linked to negative health effects. In addition, the current production of petroleum-based amines is energy and emission intensive. The present disclosure, provides, among other things, materials, methods, and products that address these negative issues.

Reaction 1 illustrates a reaction of a diamine with an aldehyde to produce a triazine:

Reaction 1

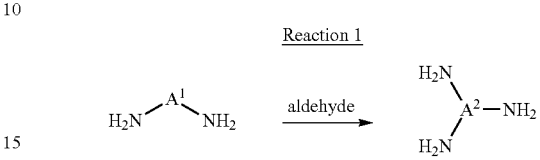

$A^1$ may include a hydrocarbon, including among other things, saturated hydrocarbon chains, unsaturated hydrocarbon chains, straight hydrocarbon chains, branched hydrocarbon chains, and/or aromatic rings. In some embodiments of the present disclosure, $A^1$ may include a heteroatom-containing ring, for example, a furan, and/or a thiophene. In some embodiments of the present disclosure, $A^1$ may include at least one of a multi-cyclic ring and/or an aromatic ring, including, for example, a naphthalene, a bicyclohexyl compound, and/or a biphenyl compound. $A^2$ may include a nitrogen-containing heterocycle, for example, a triazine group. Further, Reaction 2 illustrates the product terminating with three amine functional groups. However, the reaction may proceed further and extend the molecule to include additional $A^2$ groups (e.g., triazine groups), as long as there are additional diamine and aldehyde molecules available to react.

Reaction 2 illustrates one example of reacting a diamine with an aldehyde to form a triazine molecule, according to some embodiments of the present disclosure.

Reaction 2

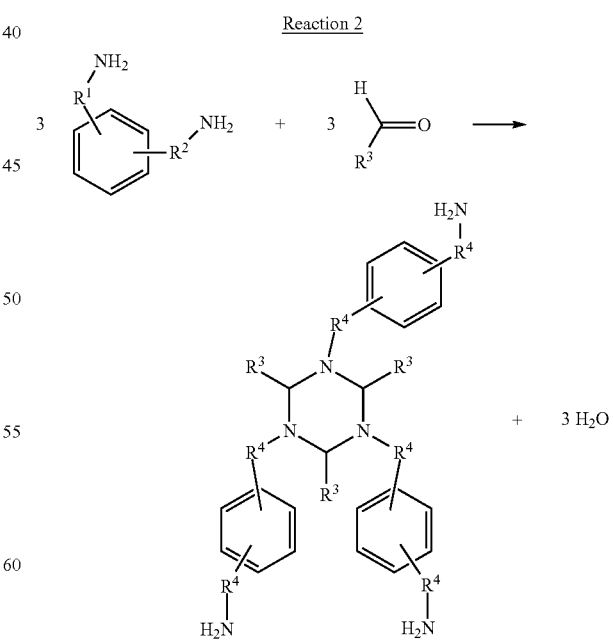

Referring to Reaction 2, in some embodiments of the present disclosure, 1e and $R^2$ may include a hydrogen atom and/or an alkane group having between 1 and 4 carbon atoms. $R^3$ may include at least one of an alkyl group, an aromatic, and/or a hydrogen atom, and $R^4$ may be either $R^1$ or $R^2$.

Reaction 3 illustrates a general reaction between an amine group and two epoxy groups resulting in a three-dimensional resin linkage, as demonstrated by the three ⁓⁓⁓⁓ bonds.

Reaction 3

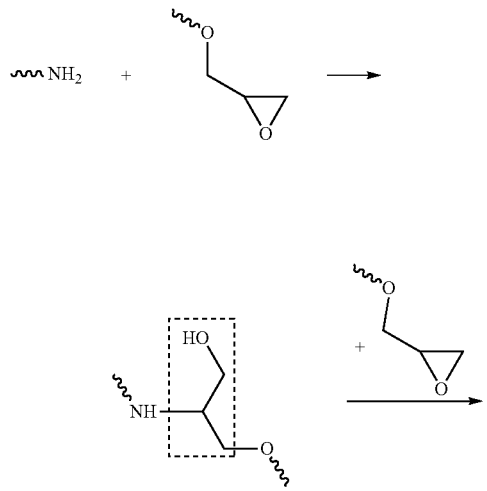

In Reaction 3, the amine groups may be supplied by the starting diamine molecule and/or by the nitrogen-containing heterocycle resulting from the reaction of a diamine with an aldehyde (as shown above in Reaction 1). Further, Reaction 3 illustrates that a single amine group may react with one or two epoxy groups to form one or two ring-opened epoxy linkages as outlined in Reaction 3 by the dotted-lines. So, for a batch reaction containing an absolute number, n, of amine functional groups, and an absolute number, m, of epoxide functional groups, the final resin's molecular weight and product distribution will depend on the ratio of n:m. For example, for the case that $2m=n$, theoretically all of the amine groups and all of the epoxy groups should react. For the case where $2m>n$, unreacted epoxy groups will exist in the reaction mixture, and for the case where $2m<n$, unreacted amine groups will remain in the reaction mixture. Reactions 4A and 4B illustrate a case where $2m=n$, for the reaction of a diamine with a second molecule having a single epoxy group.

Reaction 4A

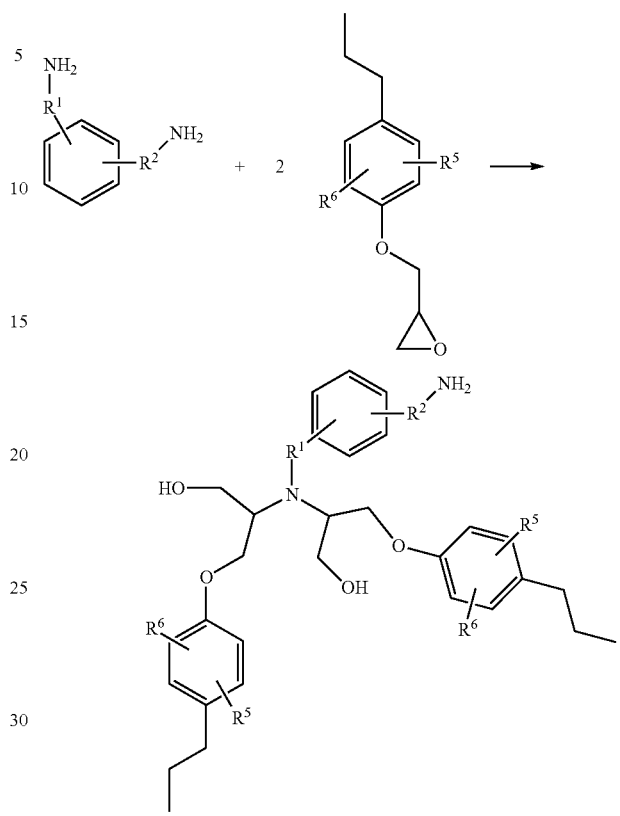

Reaction 4B

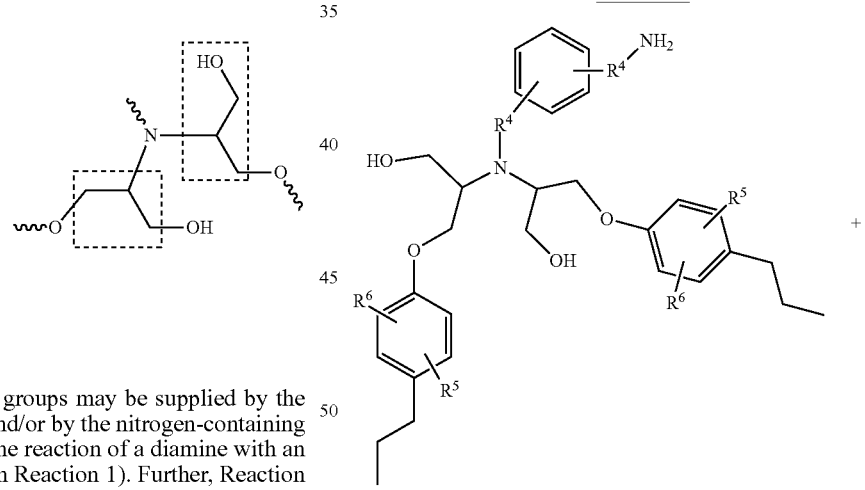

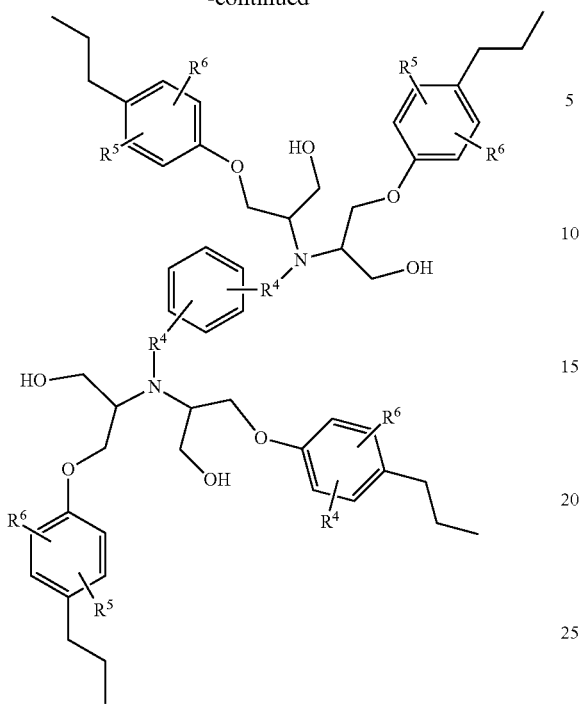

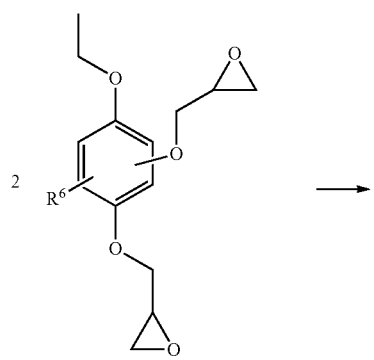

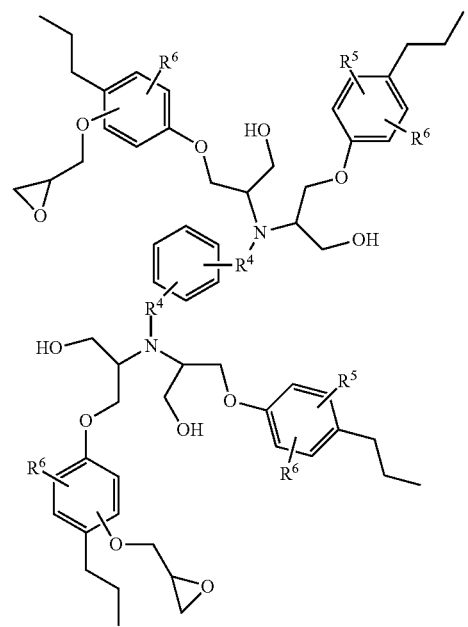

The product of Reaction 4B does not contain any additional amine groups or epoxy groups to enable additional growth to make a larger molecular weight resin. Reactions 4A and 4B further illustrate that a reaction of a diamine (or a triazine) molecule with a molecule having only a single epoxide group will result in only one step of molecular weight/size growth, at which point, the growth will terminate as no additional reactive sites are available. To enable the resin product to grow, at least some of the starting reactants should include a molecule having two or more epoxide groups. This is shown in Reaction 4C, which is equivalent to Reaction 4B except that reactants having two epoxide groups, versus just one, are used. This results in two epoxide groups remaining for further reacting with additional available amine groups; growth may continue.

Reaction 4C

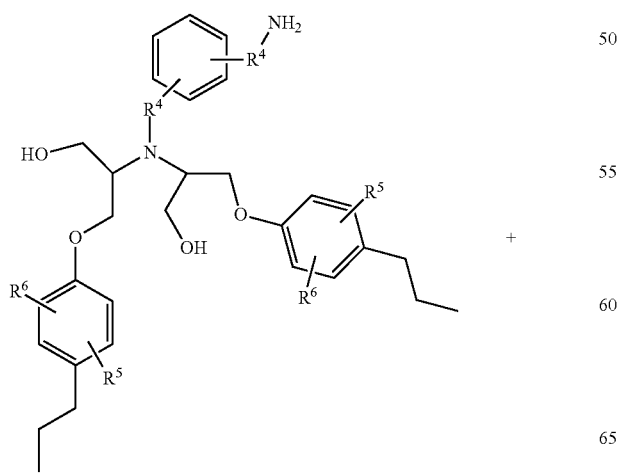

Reactions 5A, 5B, and 5C illustrate additional exemplary reactions according to some embodiments of the present disclosure, this time utilizing a dimer having two epoxy groups. Network propagation can also be achieved by synthesizing dimers of lignin-derived monomers containing two to four epoxide rings per dimer as displayed in Reactions 5A-C. Reaction 5A illustrates a limiting reaction that would inhibit additional growth in the resin product, whereas Reactions 5B and 5C illustrate routes that would preserve epoxide groups that subsequently enable additional growth of the resin.

Reaction 5A
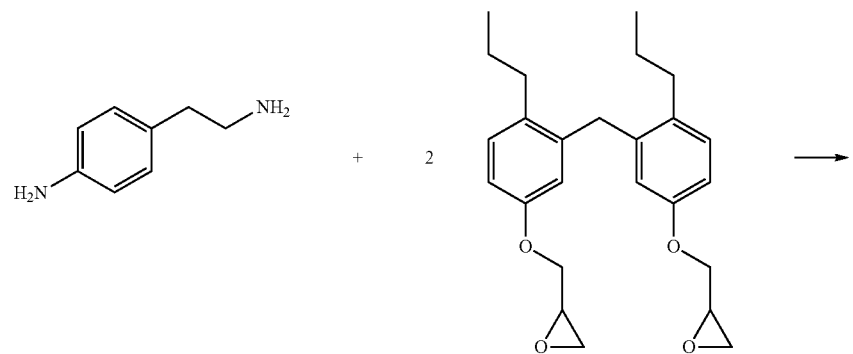
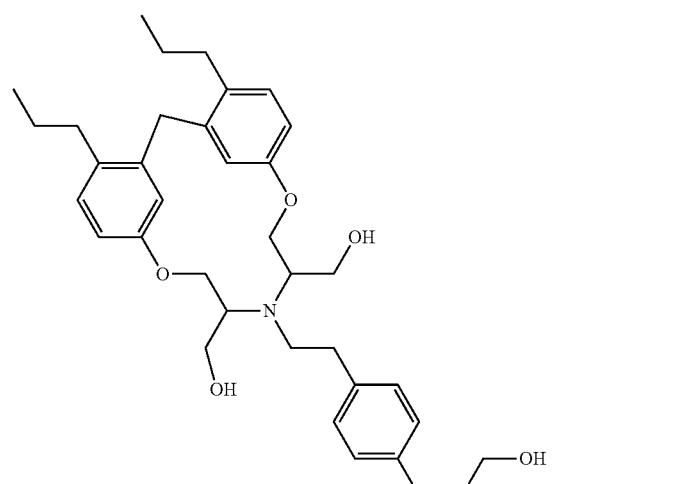
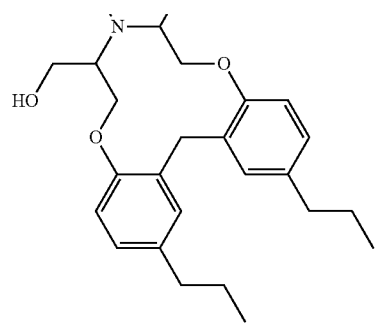
Reaction 5B
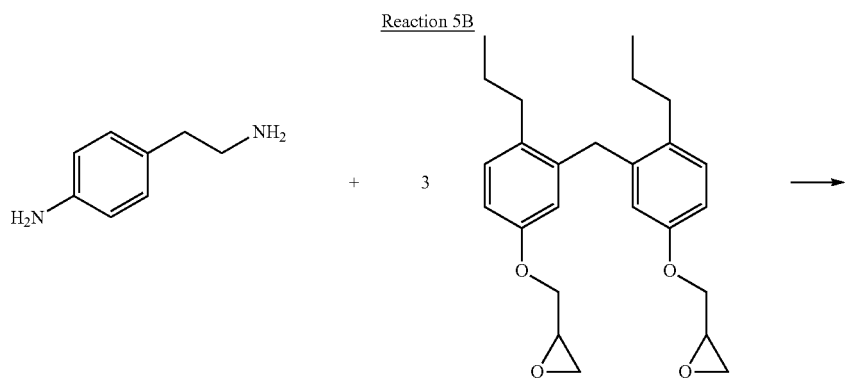

-continued
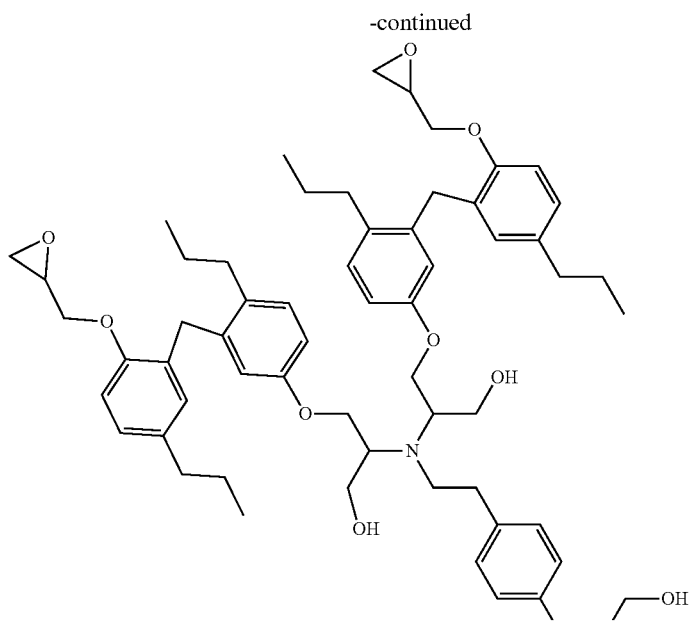
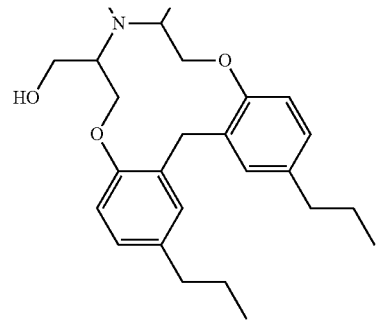
Reaction 5C
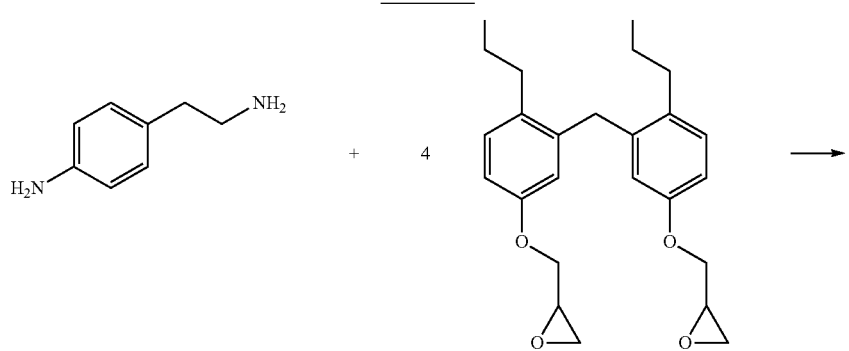

-continued

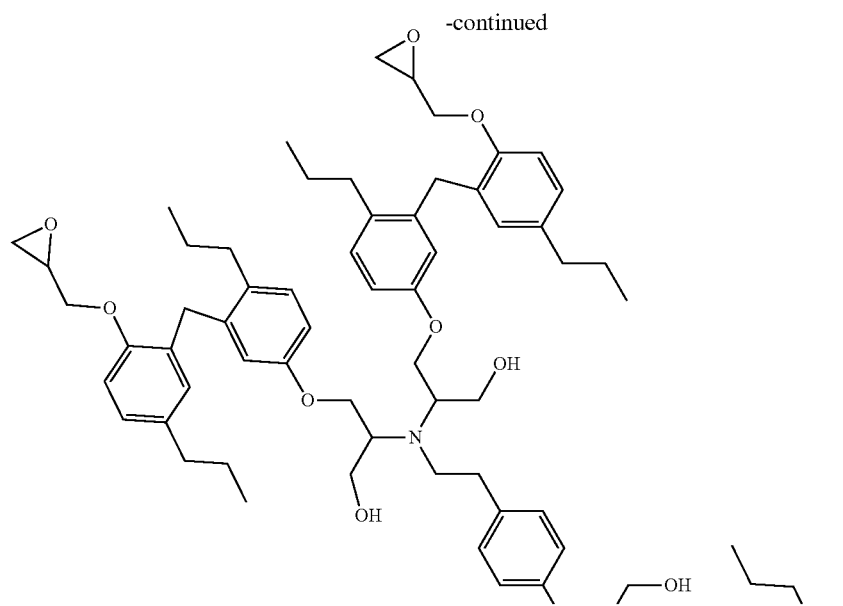

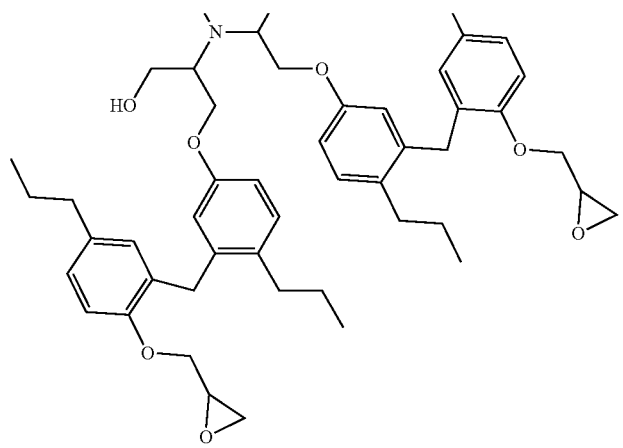

Further, at least some of the products resulting from the reactions of a diamine with a di-epoxide may be simplified as shown FIG. 1, where $A^1$ and Q are defined by the structures and language provide above and ～～～ correspond to ring-opened epoxy linkages as shown in the boxes highlighted above in Reaction 3. Similarly, FIG. 2 summarizes at least some of the products that may result from the reactions of a triazine with a di-epoxide, according to some embodiments of the present disclosure, where $A^2$ is as defined above for a triazine.

Figure 2:
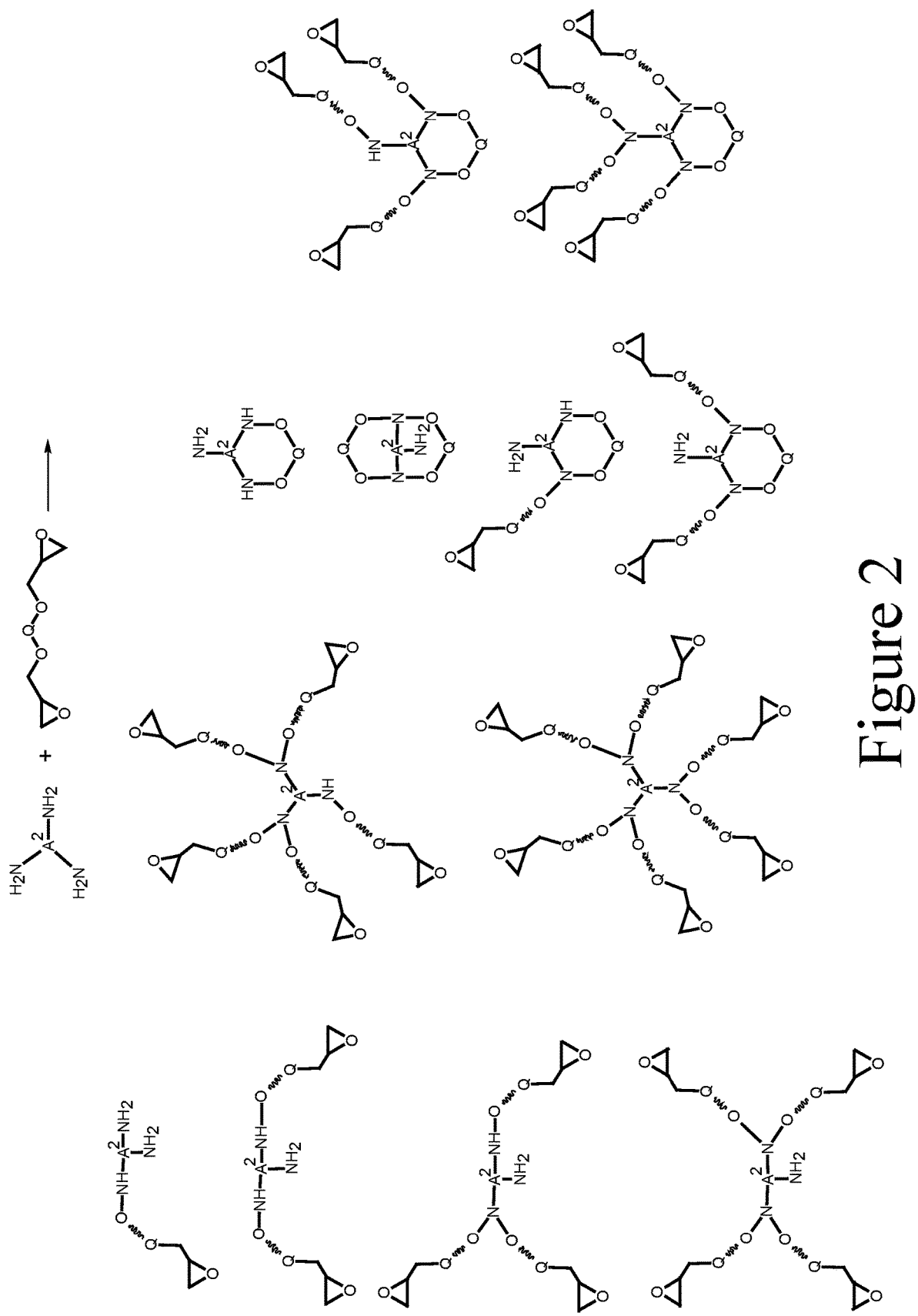
FIG. 2 illustrates a reaction of a diamine with an epoxy-containing molecule for producing a variety of larger molecules, which may be incorporated into a resin, according to some embodiments of the present disclosure.
Figure 3:
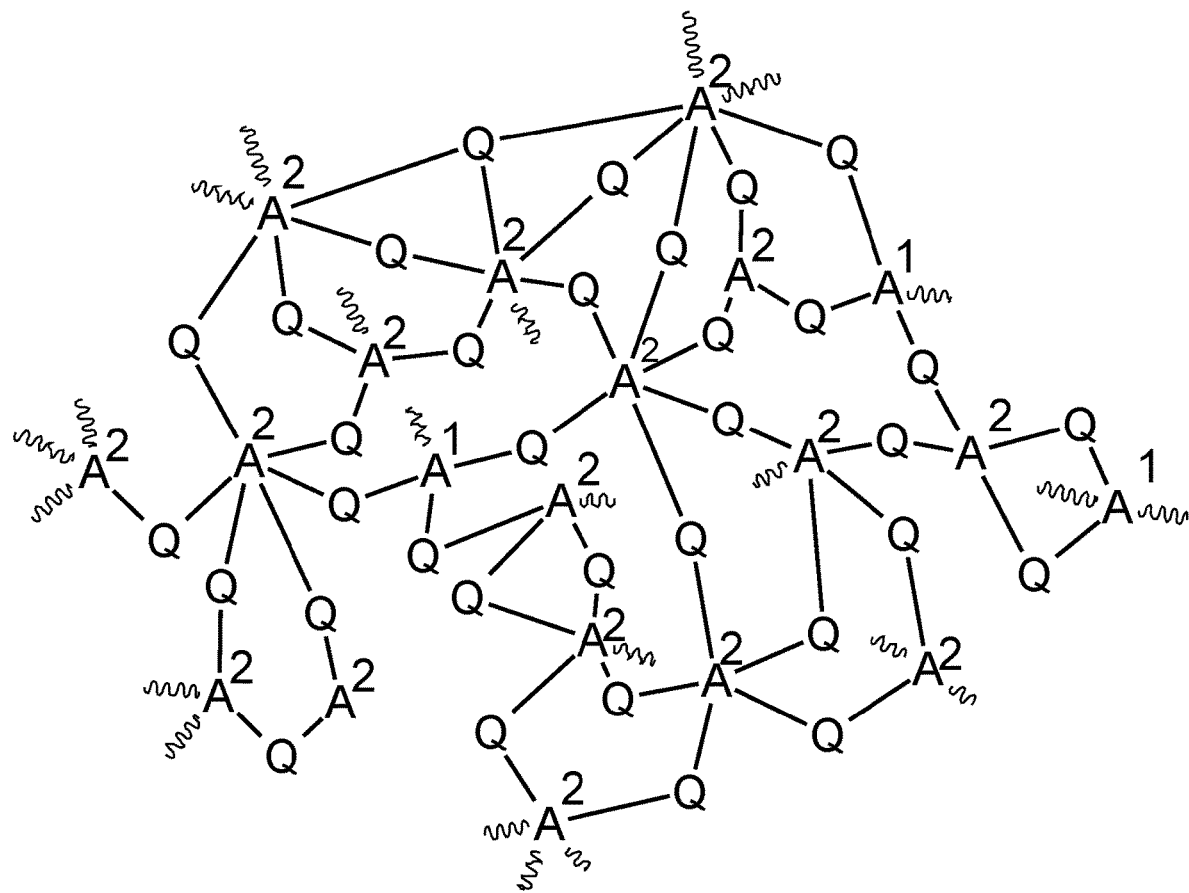
FIG. 3 illustrates a resin resulting from the larger molecules produced by reacting amine-functionalized molecules and epoxy-functionalized molecules, as illustrated in FIGS. 1 and 2 above, according to some embodiments of the present disclosure.

Thus, FIGS. 1 and 2 summarize a variety of "building blocks" that may further react to form a mixture of larger molecules and resins, as represented in FIG. 3. Each of the $A^1$ and $A^2$ groups may have all of their functional sites reacted, 4 sites and 6 sites respectively, to create between 4 and 6 ring-opened epoxy linkages with corresponding Q groups, or they may have one or more unreacted sites (e.g., unreacted hydrogen atoms positioned on amine functional groups). So, each $A^1$ group may have between 1 and 4 ring-opened epoxy linkages with between 0 and 3 unreacted hydrogen atoms. Similarly, each $A^2$ group may have between 1 and 6 ring-opened epoxy linkages with between 0 and 5 unreacted hydrogen atoms. Similarly, each Q group may have both of its epoxy groups reacted to form two ring-opened epoxy linkages to neighboring $A^1$ and/or $A^2$ groups, or a Q group may have a single epoxy linkage, with its remaining epoxy group unreacted.

EXAMPLES

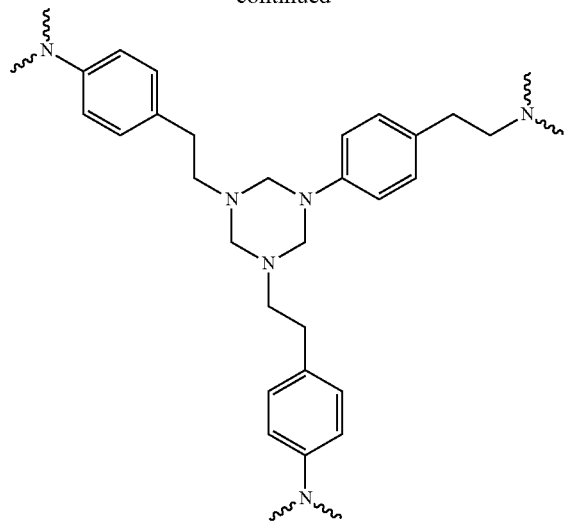

Reaction 6

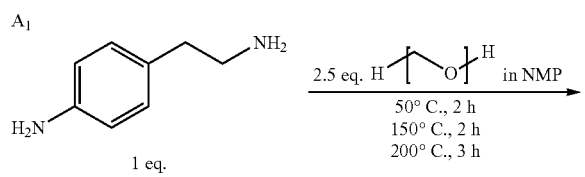

Example 1: Triazine networks as shown in Reaction 6 were formed as follows. 4-aminophenyl ethylamine (4-APEA) (0.272 g, 2 mmol) and paraformaldehyde (0.300 g, 5 mmol) were dissolved in n-methyl pyrrolidone (NMP) (3 mL, 0.67 M) and stirred at 50° C. for approximately 15 minutes and filtered through a 0.45 micron PTFE filter into a mold. The solution was cured at about 50° C. for about two hours, 50-150° C. for 2 hours, then 200° C. for 2 hours.

Reaction 7

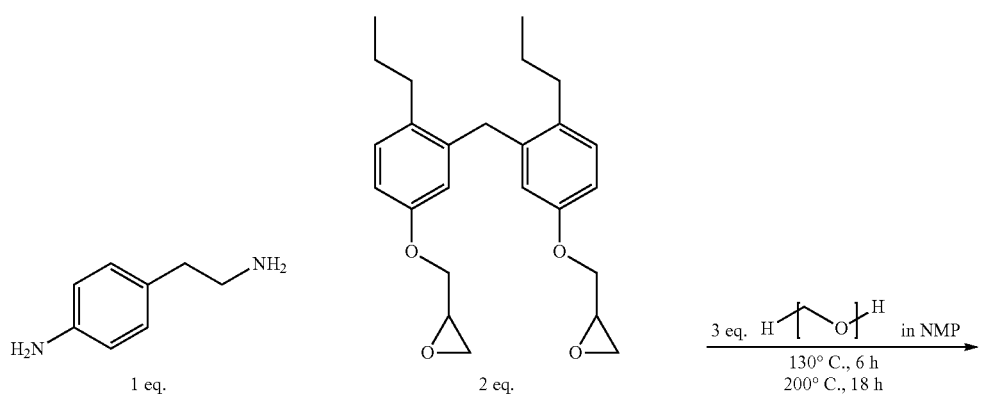

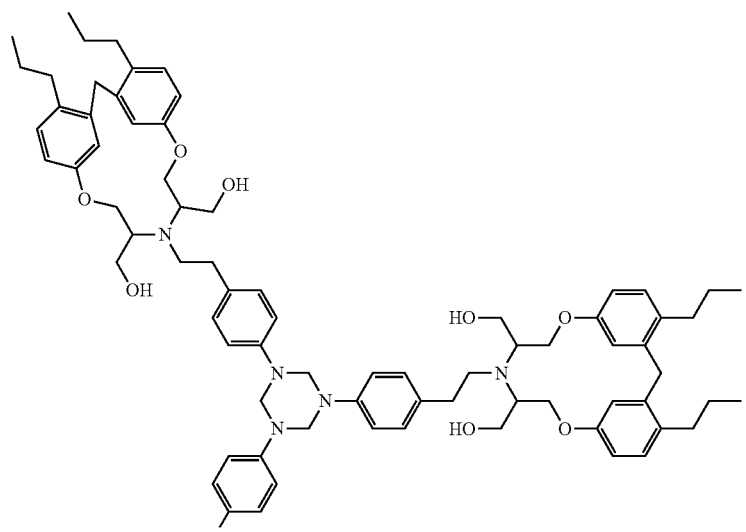

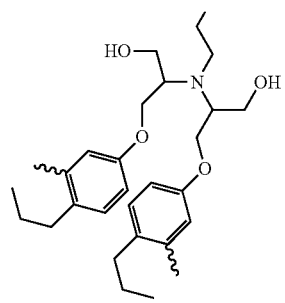

Example 2: Epoxy-triazine networks as shown in Reaction 7 were prepared in stoichiometric ratios of the epoxide to —NH₂ for curing. For example, G-dimer epoxide (1.34 g, 2.93 mmol), 4-APEA (0.200 g, 1.47 mmol), and paraformaldehyde (0.132 g, 3 eq) was dissolved in 1 mL NMP were stirred together at room temperature for ~10 minutes and degassed. The solution was cast into a mold and cured according to the following procedure: at a temperature of about 130° C. for about 6 hours, then at about 200° C. for about 18 hours.

Referring again to Reaction 7, the epoxide shown is referred to herein as an H-epoxide. Other exemplary epoxides, according to some embodiment of the present disclosure, include a G-epoxide (1 methoxy per aromatic ring always ortho- to phenol), and/or an S-epoxide (2 methoxy per aromatic ring always ortho- to phenol), which are summarized in Scheme 1 below, respectively.

Scheme 1

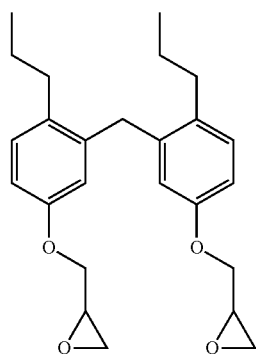

33
-continued

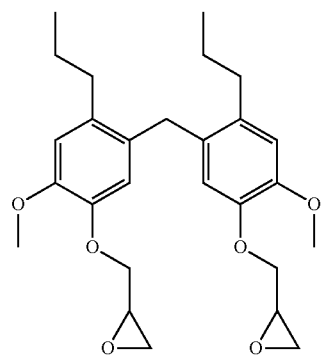

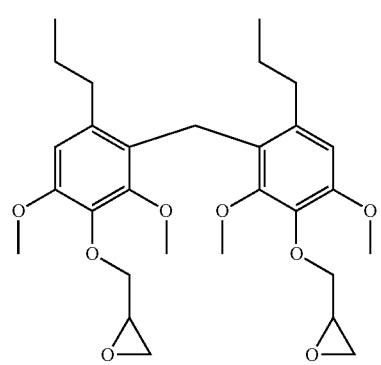

Example 3: Epoxy resins as shown in Reaction 8 were prepared in a stoichiometric ratio of epoxide to —NH for curing. Both H and S epoxide dimers are viscous oils and stirred with 4-APEA and degassed for 5 mins then cast into a mold. G epoxide dimer was typically a solid, which was lightly warmed to a viscous oil, then followed the same procedure with 4-APEA. These networks were cured according to the following procedure: 85° C. for 2 h, 105° C. for 2 h, 120° C. for 2 hours.

Reaction 8

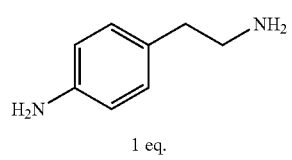

1 eq.

34
-continued

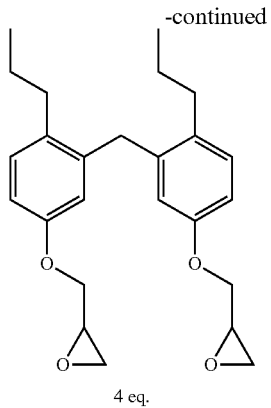

4 eq.

$\xrightarrow{\triangle}$ 85° C., 2 h
105° C., 2 h
120° C., 2 h

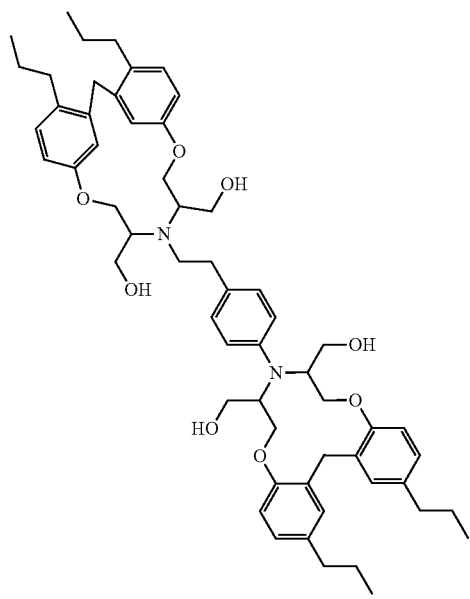

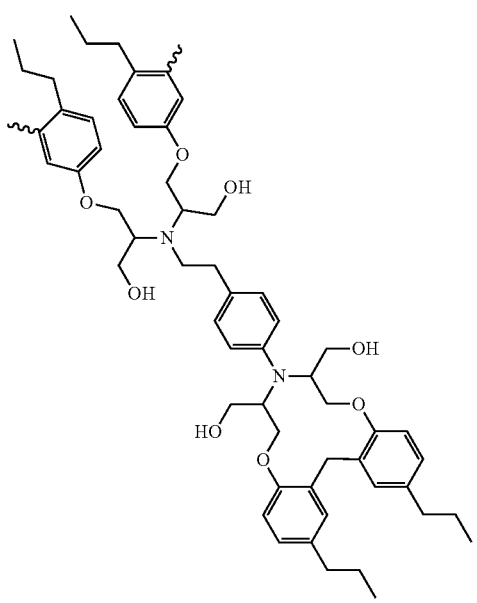

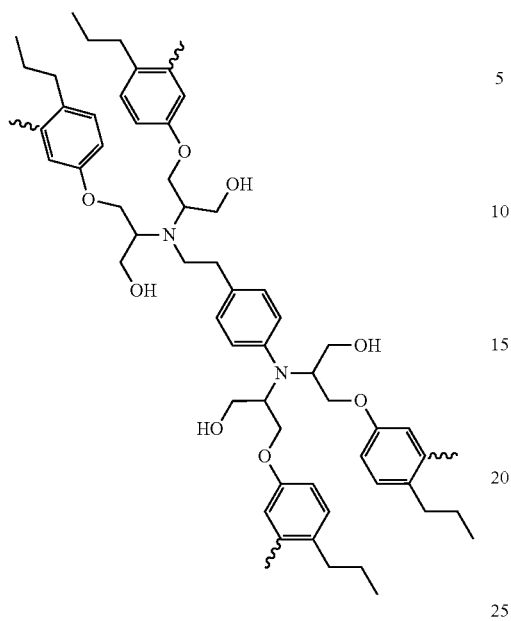
Example 4: Triazine networks were formed and reacted as illustrated in Reactions 9, 10, and 11 illustrated below.
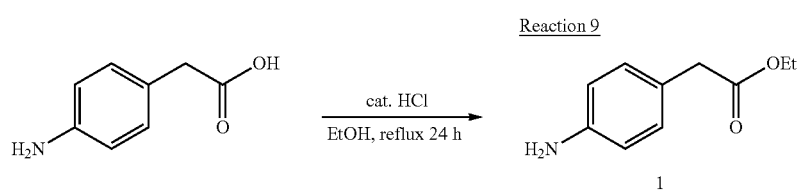
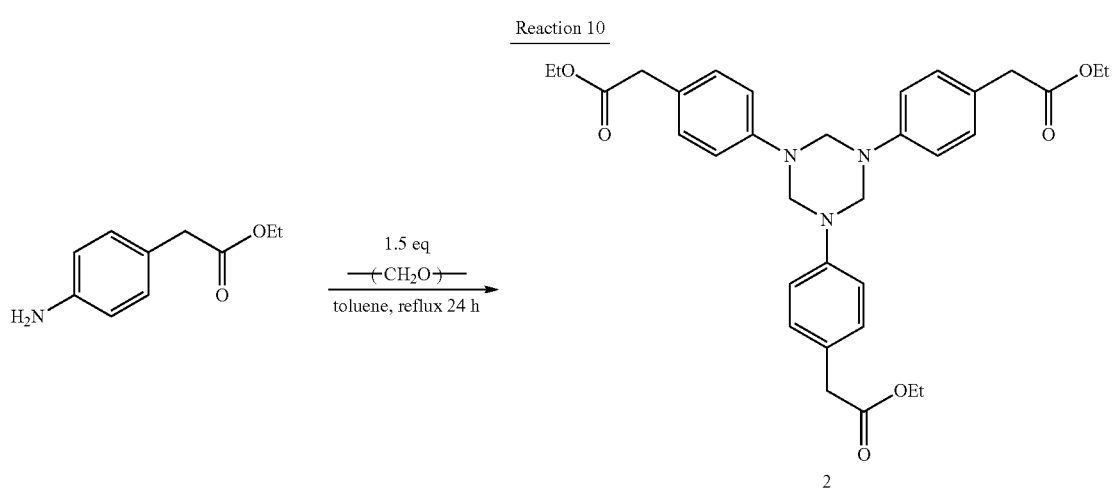

-continued
Reaction 11

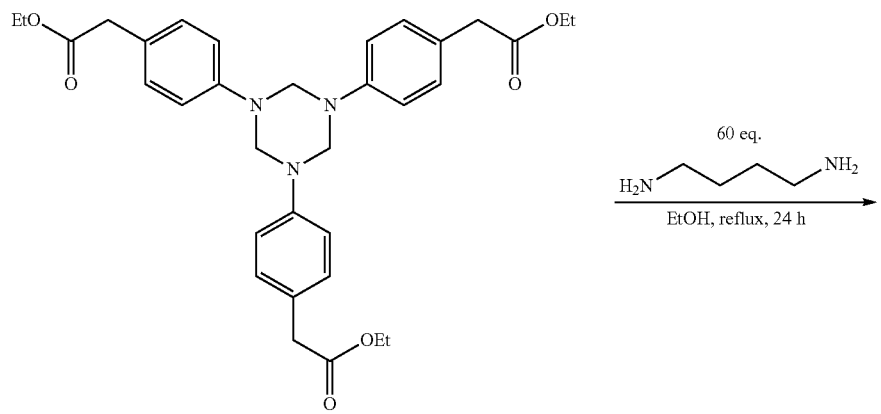

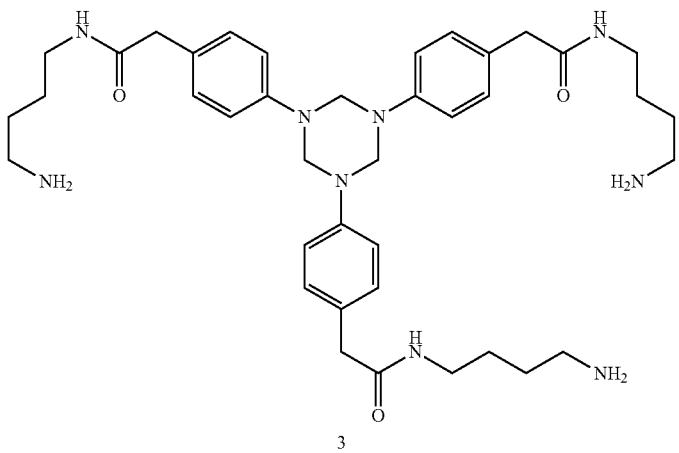

3

General Synthesis of Compound 1 shown in Reaction 9: 4-aminophenyl acetic acid was stirred in 190 proof ethanol with 5 mol % HCl catalyst. The reaction was refluxed 24 h. After 24 h, the reaction solution was cooled to room temperature and through rotary evaporation, the crude reaction was reduced to an oil. The resulting oil was redissolved in ethyl acetate (~100 mL) and extracted with saturated NaHCO$_3$ (100 mL×3), bring (100 mL), and dried over Na$_2$SO$_4$. The organic layer was then reduced to a light orange solid by rotary evaporation to yield 99.5%.

General Synthesis of Compound 2 shown in Reaction 10: Compound 1 was dissolved in toluene and 1.5 equivalents of paraformaldehyde were added. The reaction was refluxed between 6-24 h and monitored by thin layer chromatography (TLC). Once the reaction was complete, the solution was cooled to room temperature and reduced by rotary evaporation. The resultant solid was purified by flash chromatography (50% Ethyl acetate/Hexanes) to yield 90% pure Compound 2.

General synthesis of Compound 3 shown in Reaction 11: Compound 2 was refluxed in 190 proof ethanol for 24 hours with an excess (20-60 equivalents) of 1,4-diaminobutane (5M amine to ethanol). The reaction was monitored by TLC for completion. Once the reaction was complete, the solution was reduced by rotary evaporation and precipitated in diethyl ether. The white precipitate was washed with copious amounts of diethyl ether to remove excess 1,4-diamonbutane and dried overnight at 40° C. The theoretical yield of Compound 3 was about 85%.

Figure 4:
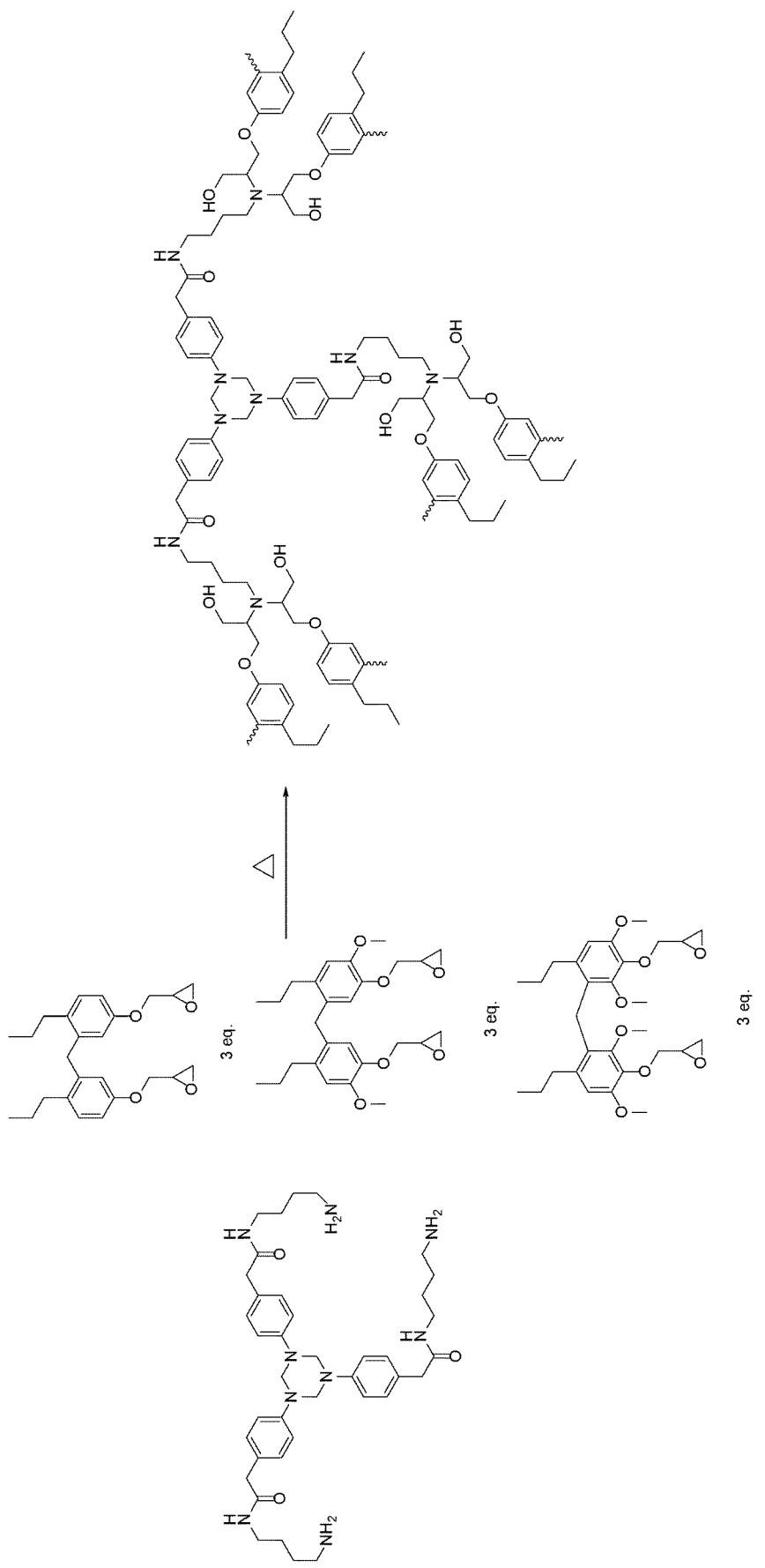
FIG. 4 illustrates a reaction of amine functional groups of a triazine molecule with reactants having epoxy functional groups, resulting in a larger molecular weight triazine molecule, according to some embodiments of the present disclosure.

Compound 3 was then reacted as illustrated in FIG. 4. Using the triazine as the amine curing agent in a 1:1 H:epoxide equivalent, the material can be mixed and degassed with nitrogen for 5 minutes. The viscous solution may then be cast in a Teflon mold and a temperature ramp will be applied (e.g., 80° C. 2 h, 150° C. 2 h, 180° C. 2 h).

Compound 2 shown in Reaction 10 may also be reacted as shown in Reaction 12 below and described below.

Reaction 12

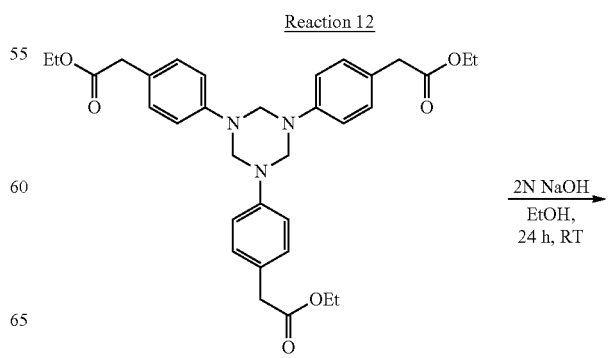

-continued

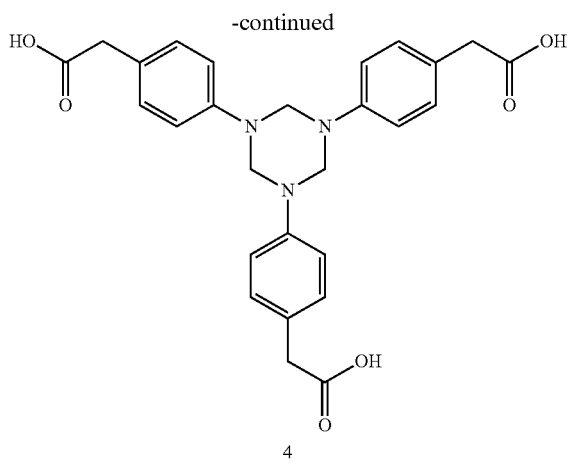

4

General synthesis of Compound 4: In an ice bath, Compound 2 was stirred in 190 proof ethanol (4 mL) and 1.5 mL of 2N NaOH was added to the solution. The reaction was stirred at 0° C. for 10 minutes, then the reaction was allowed to warm to room temperature and continued stirring for 24 hours. The crude reaction organic solvent was removed by rotary evaporation. The resulting crude solid was redissolved in DI $H_2O$ and the pH was reduced to 2 by addition of 0.1M HCl. The acidic phase was extracted with ethyl acetate (three times) and washed with brine and dried over $Na_2SO_4$. The crude organic layer was reduced to an orange solid by rotary evaporation.

Figure 5:
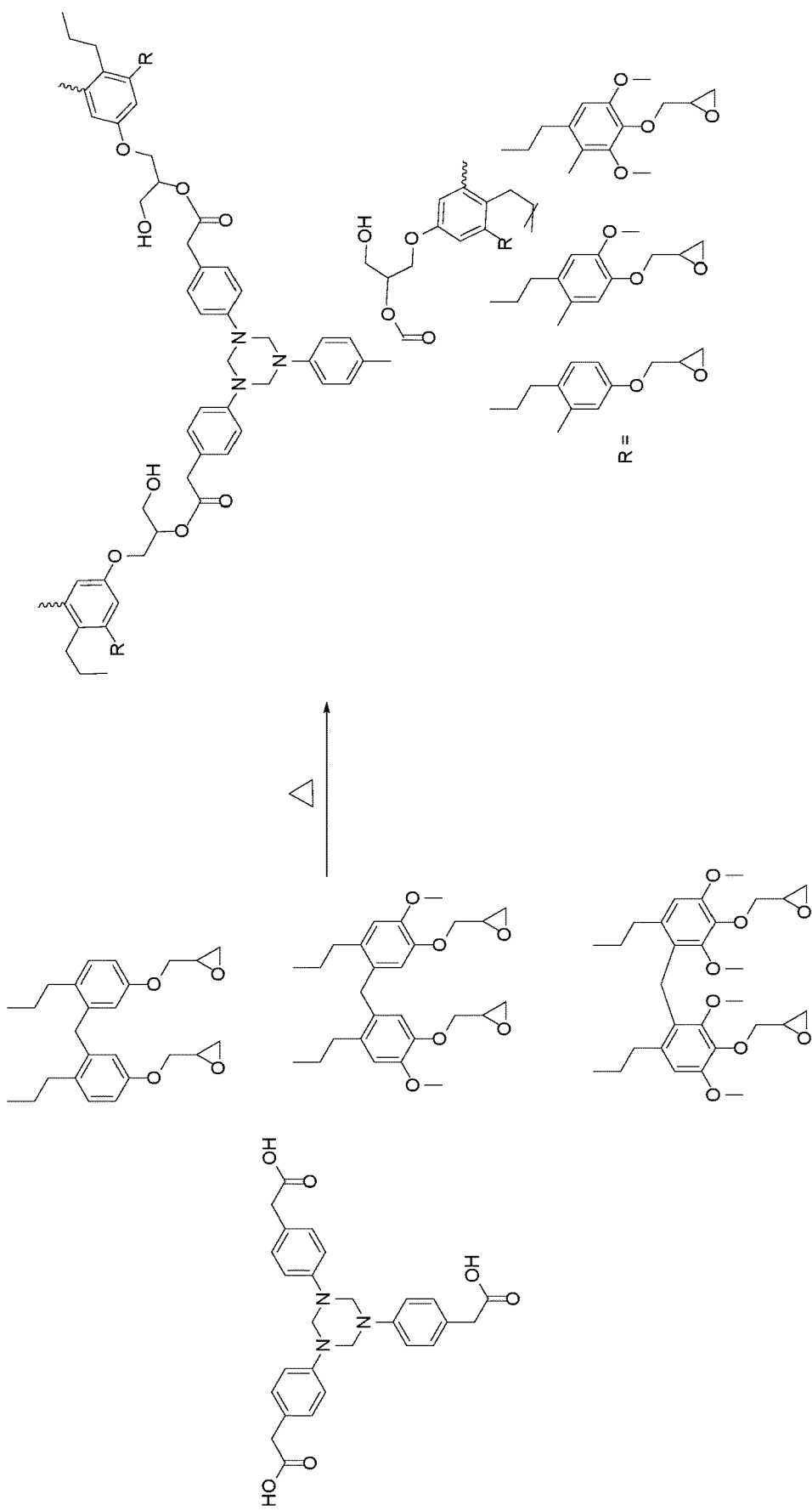
FIG. 5 illustrates a reaction of carboxylic acid functional groups of a triazine molecule with reactants having epoxy functional groups, resulting in a larger molecular weight triazine molecule, according to some embodiments of the present disclosure.

Compound 4 may then be reacted as shown in FIG. 5. Using the triazine as the acid curing agent in a 1:1 H:epoxide equivalent, the material may be mixed and degassed with nitrogen for 5 minutes. The viscous solution may be cast in a Teflon mold and a temperature ramp may be applied (e.g., 80° C. 2 h, 150° C. 2 h, 180° C. 2 h). The R group is the other side of the lignin epoxide that may be ring opened with more triazine. The structure may be fully crosslinked most likely through the 1:1 ratio of acid H:epoxide, but the structure may not allow for connecting one lignin bis(epoxide) to either end of the triazine (using 2 acid sites) because the structures can be very rigid.

Figure 6:
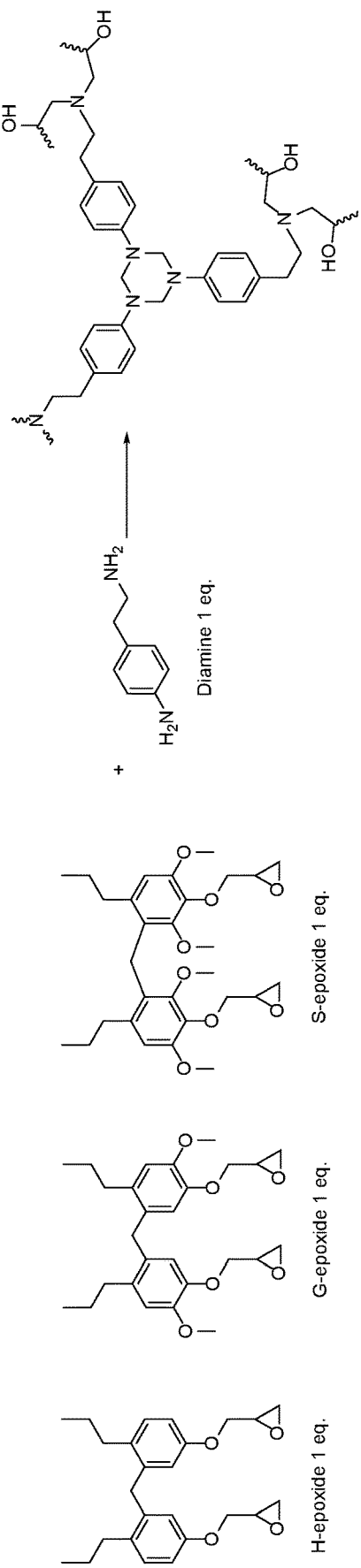
FIG. 6 illustrates a single step reaction pathway that was utilized to make a variety of degradable triazine-containing materials, according to some embodiments of the present disclosure.

Some of the triazine-containing materials described above were synthesized and their degradation in the presence of an acid tested. FIG. 6 illustrates a single step reaction pathway that was utilized to make a variety of triazine-containing materials. These materials were then degraded by immersing the materials in 1 wt % H2SO4 at 50° C. for 24 hours. The results of these degradation tests are summarized in Table 1 below.

TABLE 1 triazine degradation results

| Sample | Initial sample mass (mg) | Final sample mass (mg) | Mass loss (mg) |
|---|---|---|---|
| H epoxy triazine | 101.8 | 96.8 | 5.0 |
| G epoxy triazine | 103.4 | 92 | 11.4 |
| S epoxy triazine | 100.6 | 99.2 | 1.4 |
| G:S epoxy triazine | 104.0 | 100.1 | 3.7 |
| BADGE epoxy triazine | 101.6 | 97.3 | 4.3 |
| BADGE epoxy | 102.1 | 102.0 | 0.1 |

Whether or not a reactant or product described herein is "bioderived" may be determined by analytical methods. Using radiocarbon and isotope ratio mass spectrometry analysis, the biobased content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pMC value obtained correlates directly to the amount of biomass material present in the sample. Thus, ASTM-D866 may be used to validate that the compositions described herein are and/or are not derived from renewable sources.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A method comprising:
 a first reacting of a first molecule and formaldehyde or a paraformaldehyde to form a triazine-containing intermediate; and
 a second reacting of the triazine-containing intermediate with a second molecule comprising an epoxy group to form a triazine-containing product, wherein:
 the first molecule has a structure comprising

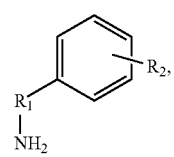

the triazine-containing intermediate has a structure comprising

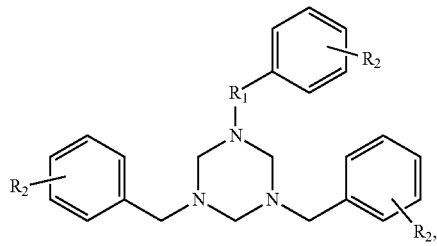

the second molecule has a structure comprising

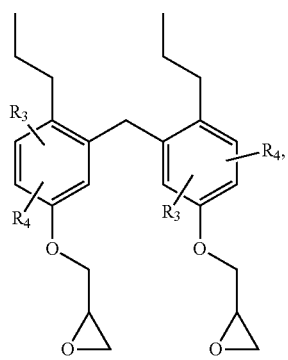

the triazine-containing product has a structure comprising

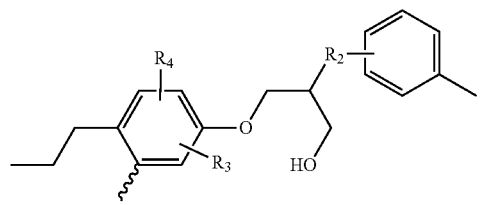

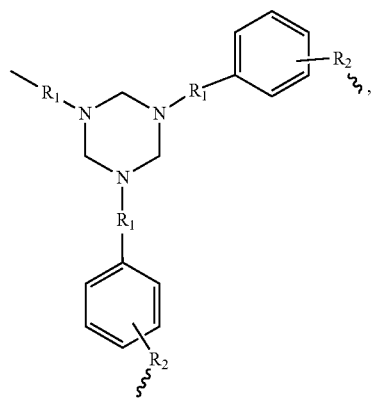

$R_1$ comprises at least one of a covalent bond or an alkyl having between 1 and 4 carbon atoms, $R_2$ is derived from at least one of an amine group, an amide group, an ester group, or a carboxylic acid group, $R_3$ comprises at least one of an alkoxy group, a hydroxyl group, an epoxide group, or a methylene group, $R_4$ comprises at least one of an alkoxy group, a hydroxyl group, an epoxide group, or a methylene group, and ⌇ represents a covalent bond to a neighboring atom.

2. The method of claim 1, wherein $R_2$ further comprises an alkyl group.

3. The method of claim 1, wherein the structure of the triazine-containing product further comprises

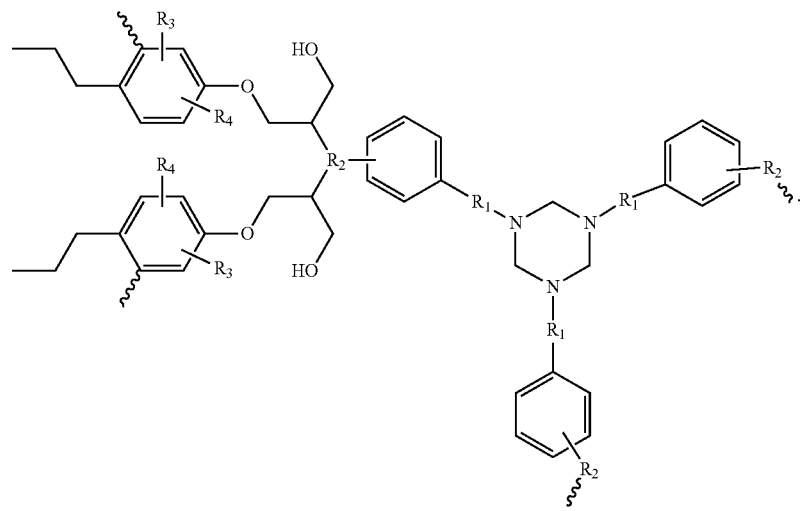

4. The method of claim 3, wherein the structure of the triazine-containing product further comprises
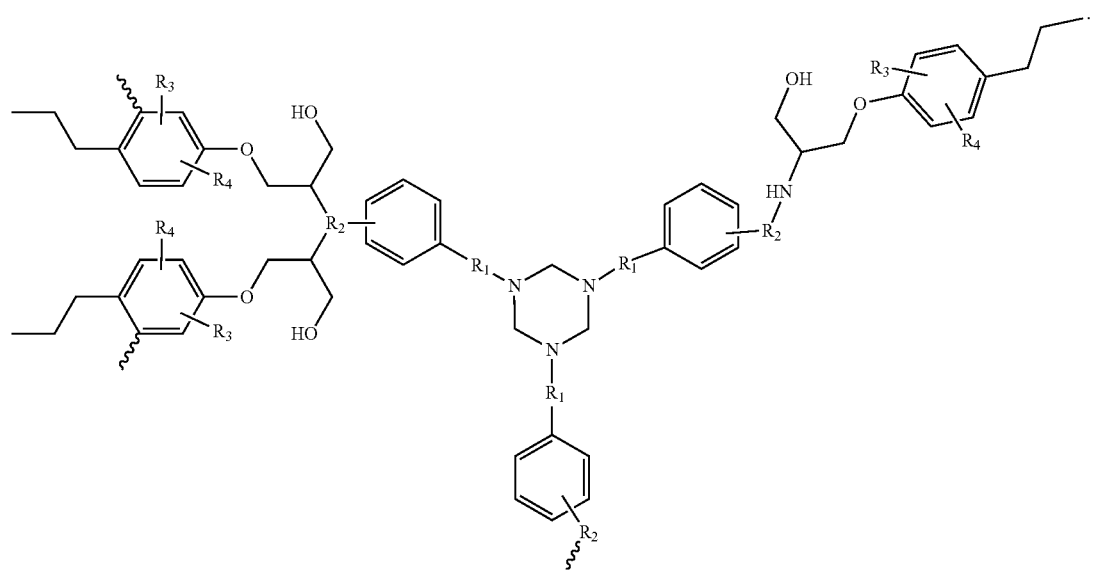
5. The method of claim 4, wherein the structure of the triazine-containing product further comprises
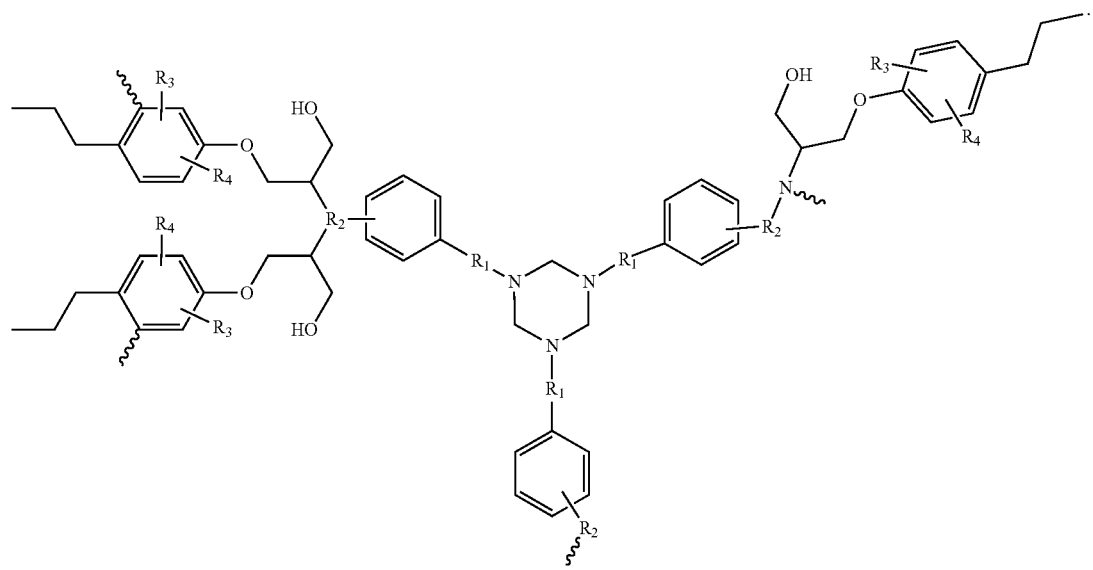

6. The method of claim 1, wherein:
the structure of the first molecule comprises

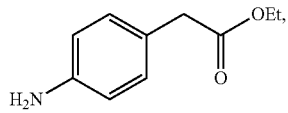

and
the structure of the triazine-containing intermediate comprises

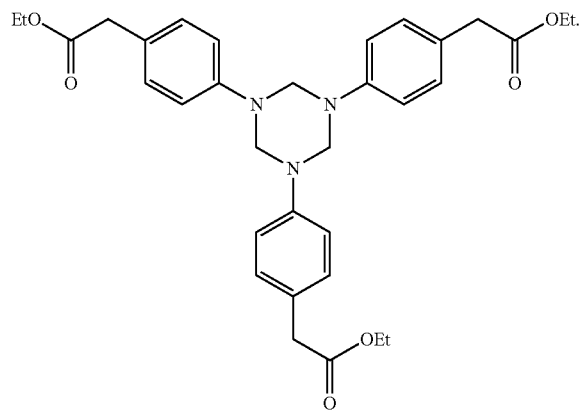 [SMILES: CCOC(=O)Cc1ccc(N2CN(c3ccc(CC(=O)OCC)cc3)CN(c3ccc(CC(=O)OCC)cc3)C2)cc1]

7. The method of claim 6, further comprising:
a third reacting of the triazine-containing intermediate with a diamine, wherein:
the diamine has a structure comprising H₂N—R—NH₂,
the third reacting transforms the triazine-containing intermediate to a structure comprising

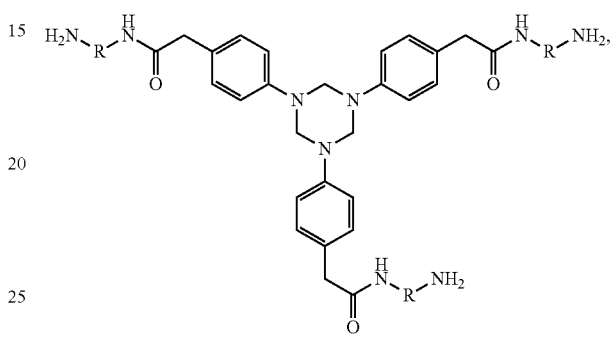

and
R comprises an alkyl group having between 1 and 10 carbon atoms.

8. The method of claim 7, wherein the second reacting forms the triazine-containing product having a structure comprising

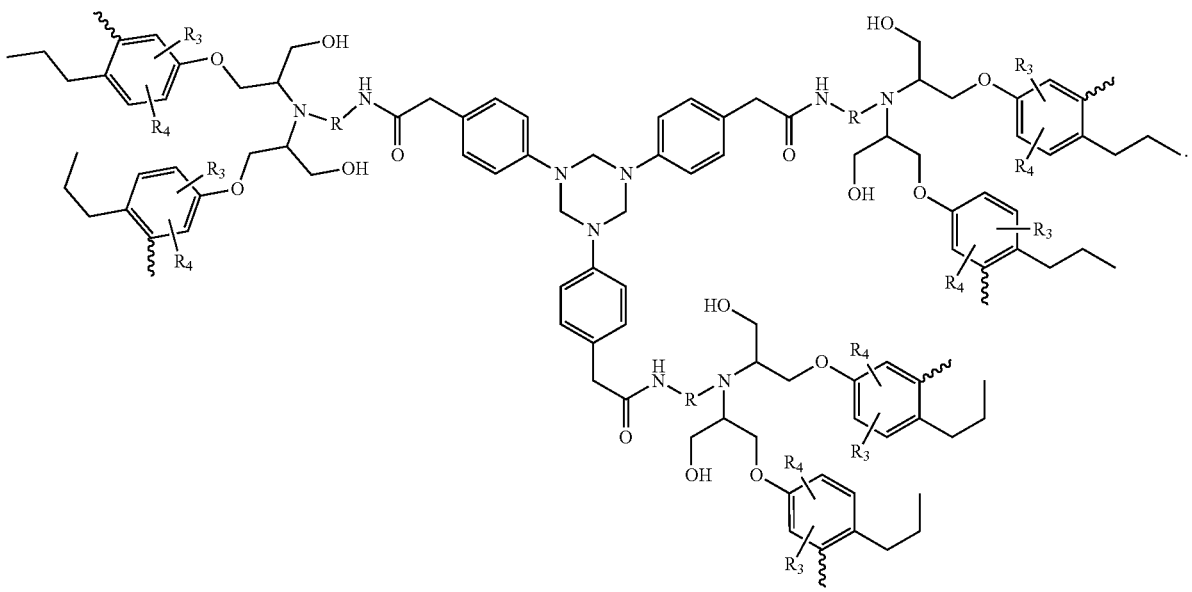

9. The method of claim 6, further comprising:
a fourth reacting of the triazine-containing intermediate with a base, wherein:
the fourth reacting transforms the triazine-containing intermediate to a structure comprising
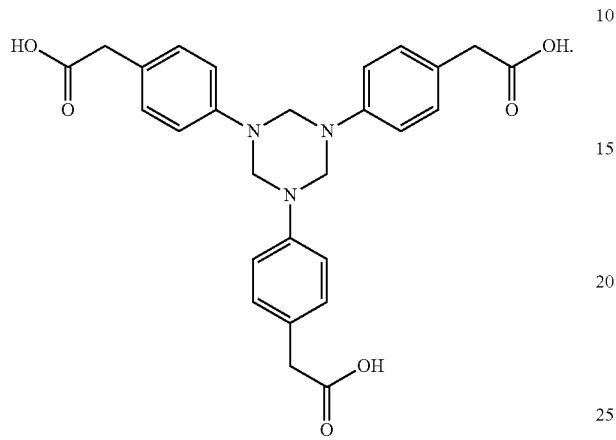
10. The method of claim 9, wherein the second reacting forms the triazine-containing product having a structure comprising
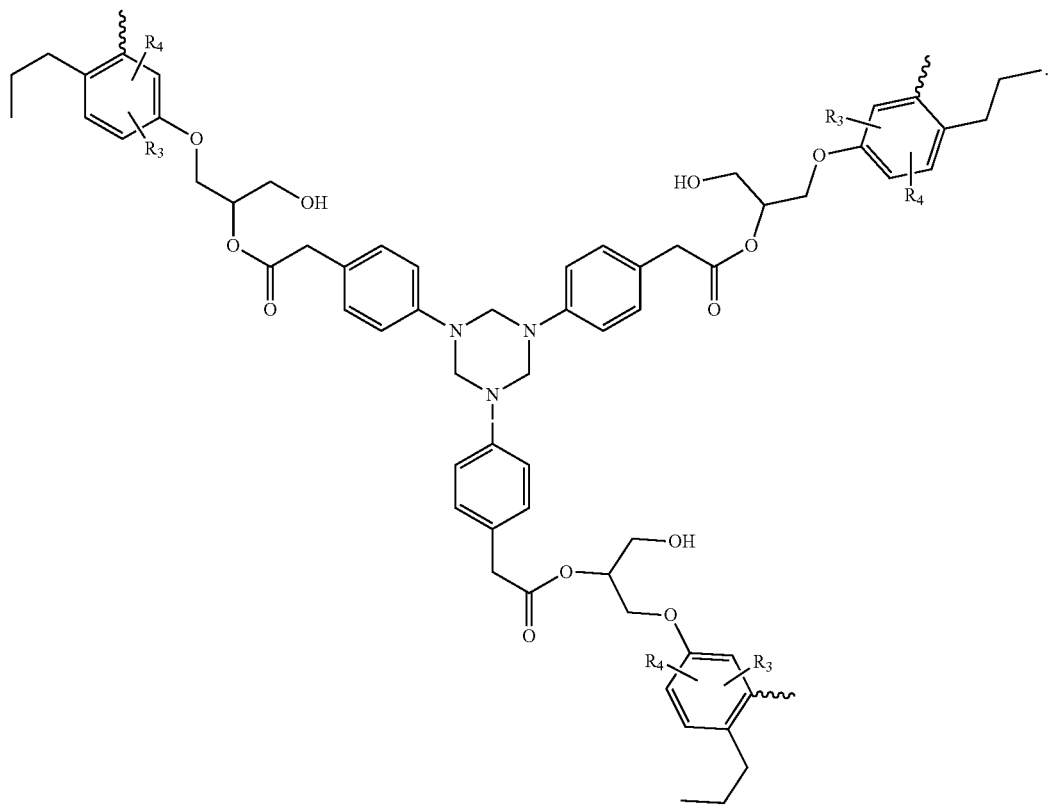

11. The method of claim 1, wherein at least one of the first molecule or the second molecule is bioderived.

12. The method of claim 1, wherein the triazine-containing produce is biodegradable.

13. A composition comprising:
the structure

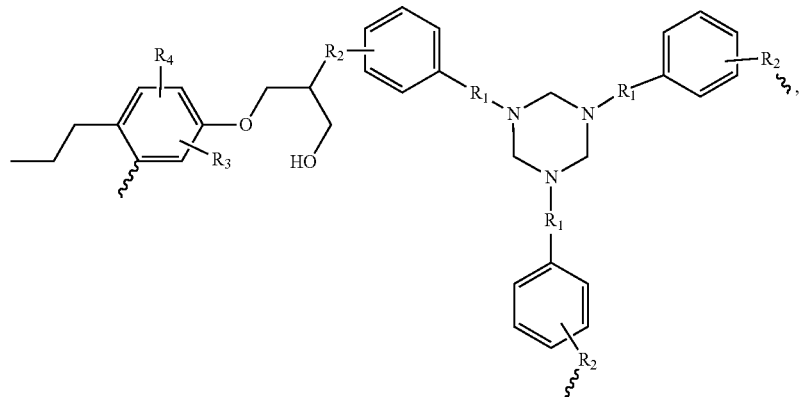

wherein:
$R_1$ comprises at least one of a covalent bond or an alkane having between 1 and 4 carbon atoms,
$R_2$ comprises at least one of an amine group, an amide group, an ester group, or a carboxylic acid group,
$R_3$ comprises at least one of an alkoxy group, a hydroxyl group, an epoxide group, or a methylene group, $R_4$ comprises at least one of an alkoxy group, a hydroxyl group, an epoxide group, or a methylene group, and ⁓ represents a covalent bond to a neighboring atom.

14. The composition of claim 13, wherein:
the structure further comprises

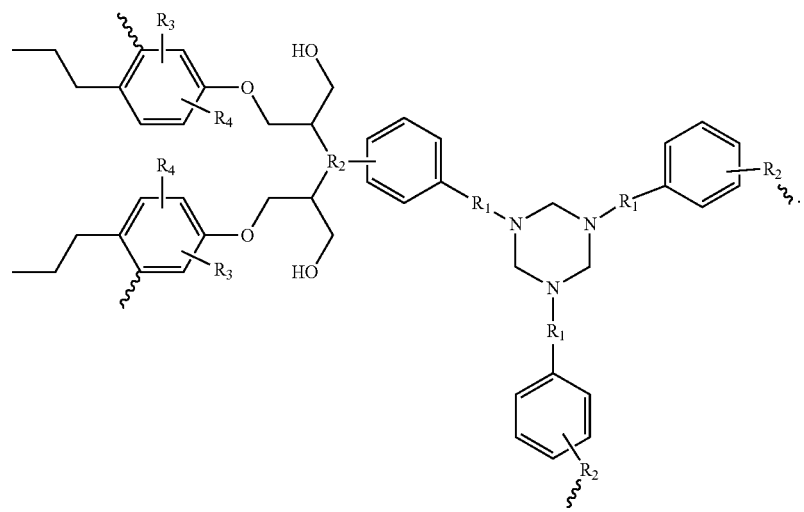

15. The composition of claim 14, wherein:
the structure further comprises
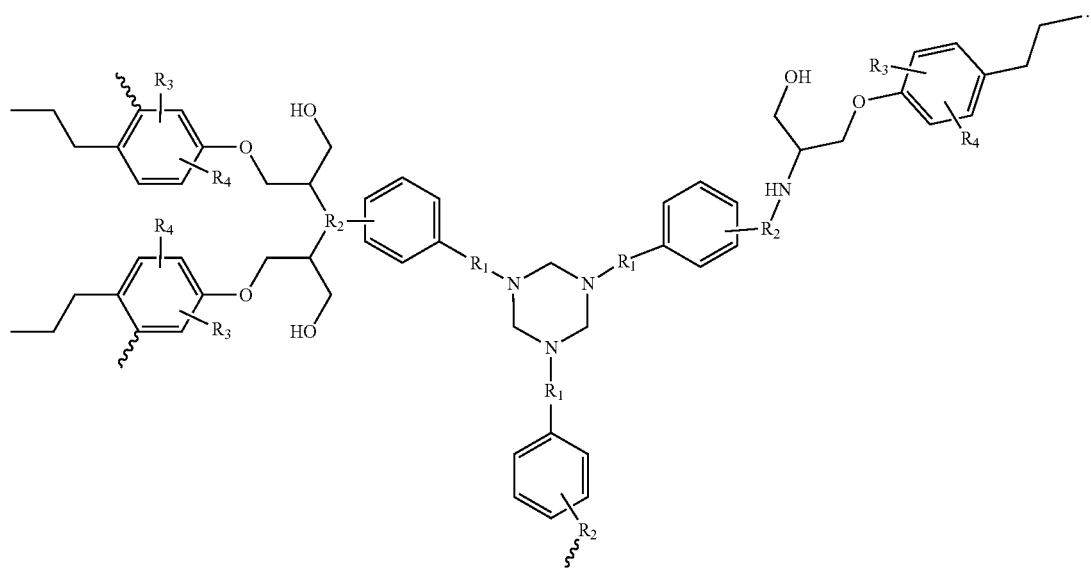
16. The composition of claim 15, wherein:
the structure further comprises
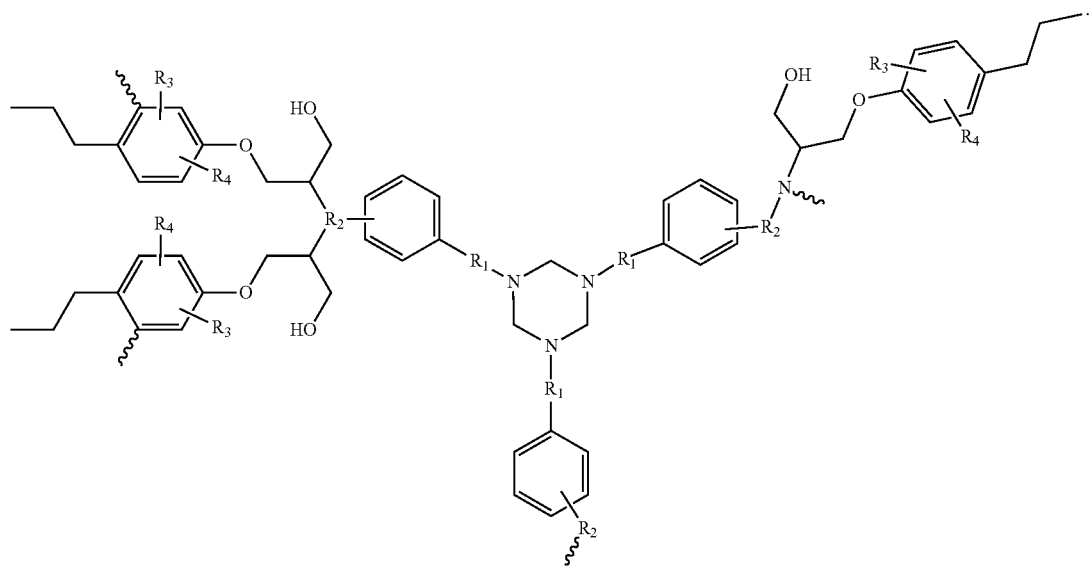

17. The composition of claim 13, wherein:
the structure comprises
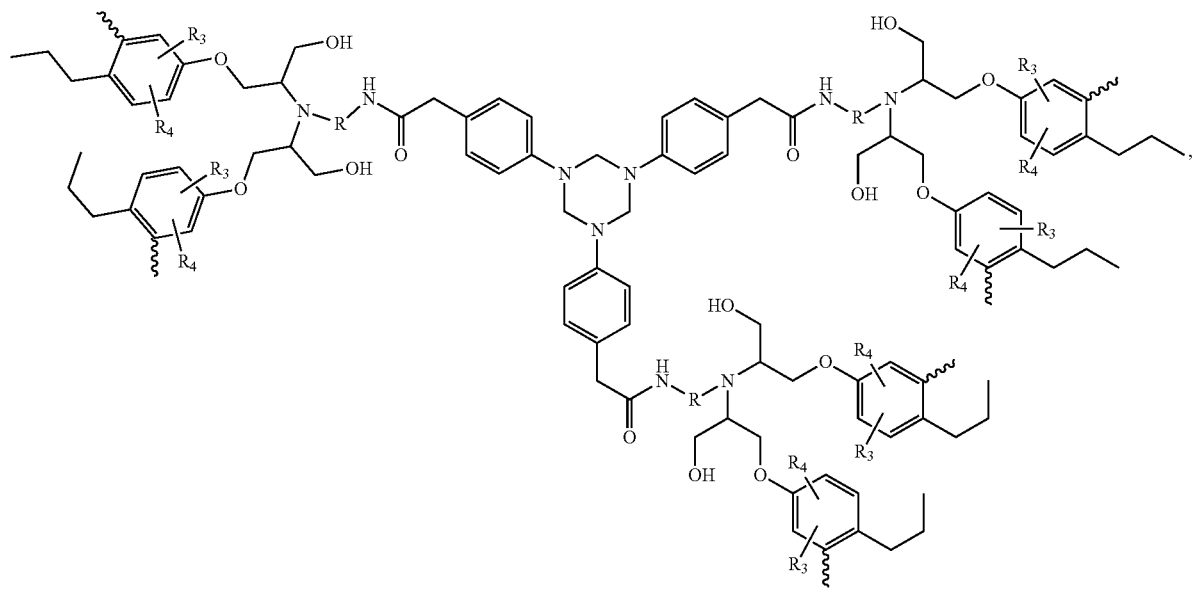
wherein:
R comprises an alkyl group having between 1 and 10 carbon atoms.
18. The composition of claim 13, wherein:
the structure comprises
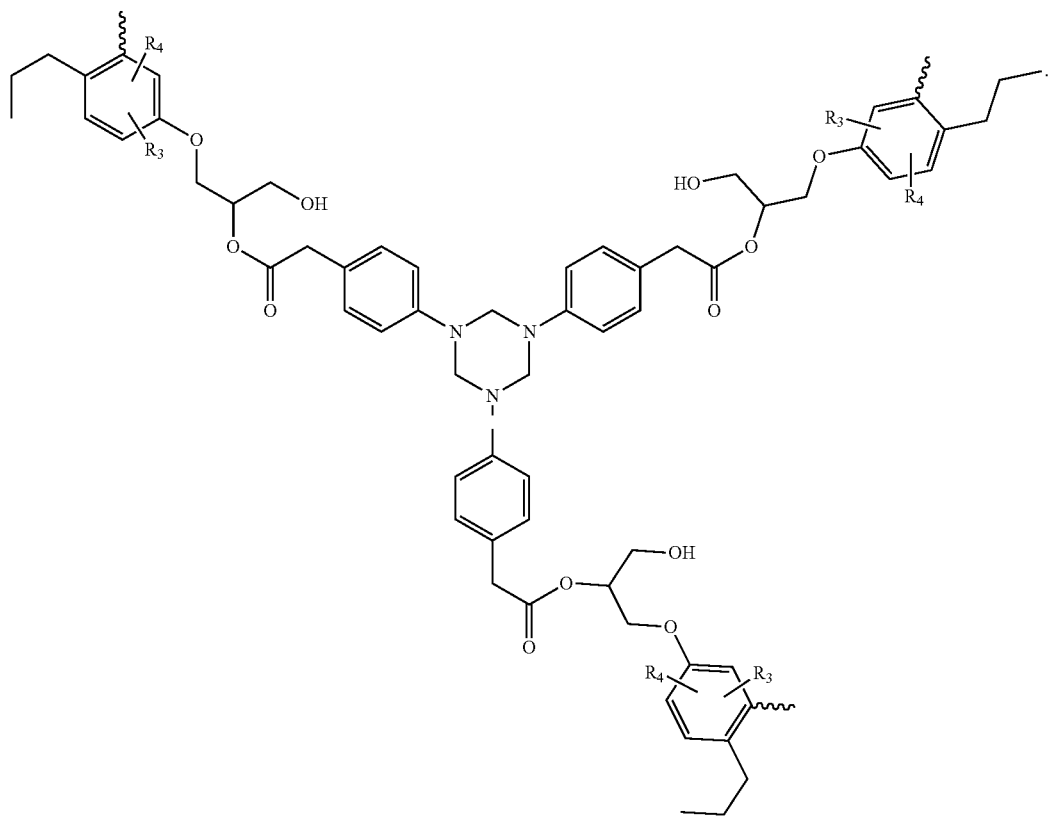

19. The composition of claim 13, wherein at least a portion of the composition is bioderived.

20. The composition of claim 13, wherein composition is biodegradable.

* * * * *